(12) United States Patent
Eaves et al.

(10) Patent No.: US 11,141,121 B2
(45) Date of Patent: Oct. 12, 2021

(54) FLUOROSCOPE WITH MOVABLE HEAD AND BARRIER TO VARY SOURCE TO SKIN DISTANCE

(71) Applicant: Onyx Technical Consulting, LLC, Scottsdale, AZ (US)

(72) Inventors: Christopher Eaves, Scottsdale, AZ (US); Daniel G. Reed, Mesa, AZ (US); James F. Reed, Mesa, AZ (US)

(73) Assignee: Onyx Technical Consulting, LLC, Scottsdale, AZ (US)

( * ) Notice: Subject to any disclaimer, the term of this patent is extended or adjusted under 35 U.S.C. 154(b) by 0 days.

(21) Appl. No.: 16/219,822

(22) Filed: Dec. 13, 2018

(65) Prior Publication Data

US 2019/0175128 A1    Jun. 13, 2019

Related U.S. Application Data

(63) Continuation-in-part of application No. PCT/US2018/037409, filed on Jun. 13, 2018.
(Continued)

(51) Int. Cl.
*A61B 6/00* (2006.01)
*H05G 1/02* (2006.01)
(Continued)

(52) U.S. Cl.
CPC ............ *A61B 6/487* (2013.01); *A61B 6/4225* (2013.01); *A61B 6/4441* (2013.01);
(Continued)

(58) Field of Classification Search
CPC ..... A61B 6/487; A61B 6/4225; A61B 6/4441; A61B 6/4452; A61B 6/584; A61B 6/107; A61B 6/547; H05G 1/02; H05G 1/04
See application file for complete search history.

(56) References Cited

U.S. PATENT DOCUMENTS 2,223,451 A * 12/1940 Jones ...................... B23K 7/06
                                                   266/53
3,724,679 A *  4/1973 Brownell ................ B66C 23/90
                                                   212/278
(Continued)

FOREIGN PATENT DOCUMENTS

WO    2017009398 A1    1/2017
WO    2018232037 A1    12/2018

OTHER PUBLICATIONS

USPTO, International Search Report and Written Opinion for International Patent Application No. PCT/US2018/037409, dated Sep. 13, 2018. 8 pages.
(Continued)

*Primary Examiner* — Blake C Riddick
(74) *Attorney, Agent, or Firm* — Perkins Coie LLP

(57) ABSTRACT

For radiation safety, a fluoroscope has an adjustable X-ray source-to-intensifier distance (SID) and an X-ray transparent spacer positioned between the source and receptor. As a distance between the source and the intensifier is changed, the spacer is moved or a different sized transparent spacer is used, to ensure a safe minimum skin-to-source distance (SSD) is maintained. A processor is programmed to inhibit the generation of X-rays if the SID is greater than a defined distance and the spacer is not in position.

12 Claims, 20 Drawing Sheets

Related U.S. Application Data

(60) Provisional application No. 62/519,707, filed on Jun. 14, 2017.

(51) Int. Cl.
*H05G 1/04* (2006.01)
*A61B 6/10* (2006.01)

(52) U.S. Cl.
CPC ............ *A61B 6/4452* (2013.01); *A61B 6/584* (2013.01); *H05G 1/02* (2013.01); *H05G 1/04* (2013.01); *A61B 6/107* (2013.01); *A61B 6/547* (2013.01)

(56) References Cited

U.S. PATENT DOCUMENTS

| | | | | |
|---|---|---|---|---|
| 3,892,967 | A * | 7/1975 | Howarth | A61B 6/4441 378/197 |
| 3,927,326 | A * | 12/1975 | Kunne | A61B 6/4452 378/179 |
| 3,984,693 | A * | 10/1976 | Tomita | A61B 6/02 378/25 |
| 4,144,460 | A * | 3/1979 | Norman | A61B 6/14 378/170 |
| 4,221,970 | A * | 9/1980 | Ciavattoni | A61B 6/0478 378/168 |
| 4,358,856 | A * | 11/1982 | Stivender | A61B 6/4283 378/167 |
| 4,805,202 | A | 2/1989 | Deucher et al. | |
| 4,856,036 | A | 8/1989 | Malcolm et al. | |
| 5,627,873 | A * | 5/1997 | Hanover | A61B 6/4405 378/196 |
| 5,642,395 | A * | 6/1997 | Anderton | A61B 6/4225 378/197 |
| 5,720,679 | A * | 2/1998 | Schroeder | A63B 63/083 473/484 |
| 5,823,120 | A * | 10/1998 | Holmquist | A47B 9/02 108/147 |
| 7,810,996 | B1 | 10/2010 | Giphart et al. | |
| 8,880,153 | B2 * | 11/2014 | Pfister | A61B 6/12 600/431 |
| 9,161,727 | B2 | 10/2015 | Jenkins et al. | |
| 9,872,659 | B2 * | 1/2018 | Jenkins | A61B 6/487 |
| 10,271,807 | B2 * | 4/2019 | Jenkins | A61B 6/06 |
| 10,285,660 | B2 | 5/2019 | Zaiki et al. | |
| 10,687,771 | B2 | 6/2020 | Uehara et al. | |
| 2002/0085681 | A1 * | 7/2002 | Jensen | A61B 6/463 378/197 |
| 2005/0002489 | A1 | 1/2005 | Scheuering | |
| 2006/0181417 | A1 * | 8/2006 | Pullmann | H03K 17/9502 340/545.2 |
| 2006/0269044 | A1 | 11/2006 | Fehre et al. | |
| 2007/0140429 | A1 | 6/2007 | Hoheisel | |
| 2007/0237309 | A1 | 10/2007 | Marinelli et al. | |
| 2008/0095306 | A1 * | 4/2008 | Jensen | A61B 6/467 378/10 |
| 2008/0118023 | A1 * | 5/2008 | Besson | A61B 6/4028 378/8 |
| 2009/0024025 | A1 * | 1/2009 | Maschke | A61B 6/4464 600/425 |
| 2009/0232282 | A1 * | 9/2009 | Belson | A61B 6/107 378/203 |
| 2012/0148031 | A1 | 6/2012 | Eaves | |
| 2013/0089183 | A1 | 4/2013 | Sura | |
| 2013/0243153 | A1 | 9/2013 | Sra | |
| 2014/0192962 | A1 | 7/2014 | Eaves | |
| 2015/0201796 | A1 * | 7/2015 | Kuempel | H04L 67/10 426/231 |
| 2015/0313666 | A1 * | 11/2015 | Aljuri | A61B 18/12 606/41 |
| 2015/0320375 | A1 * | 11/2015 | De Jong | A61B 6/4291 378/63 |
| 2015/0342548 | A1 | 12/2015 | Zaiki | |
| 2015/0362088 | A1 * | 12/2015 | Marco | F16K 31/084 335/229 |
| 2016/0174915 | A1 | 6/2016 | Odea | |
| 2018/0035523 | A1 * | 2/2018 | Diehm | A61B 6/4007 |

OTHER PUBLICATIONS

USPTO, International Preliminary Report on Patentability, for International Patent Application No. PCTUS2018/037409, dated Sep. 6, 2019. 14 pages.

European Patent Office, Extended European Search Report, EP Patent Application 18817552.5, dated Jan. 29, 2021, 7 pages.

Kim (KR 10-457099 B1), 2014. Machine translation of Tube Supporter of 3D Digital Radiography System, 14 pages.

* cited by examiner

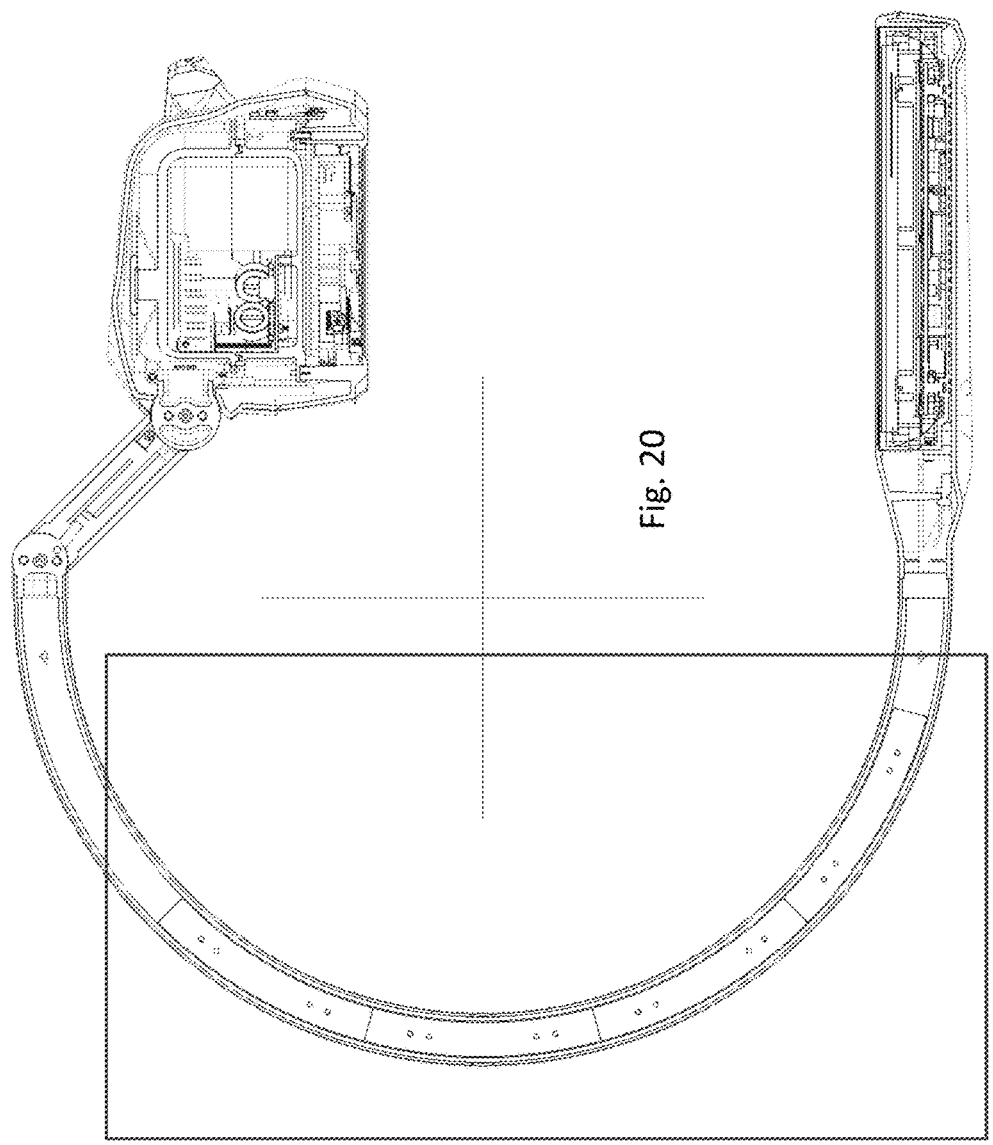
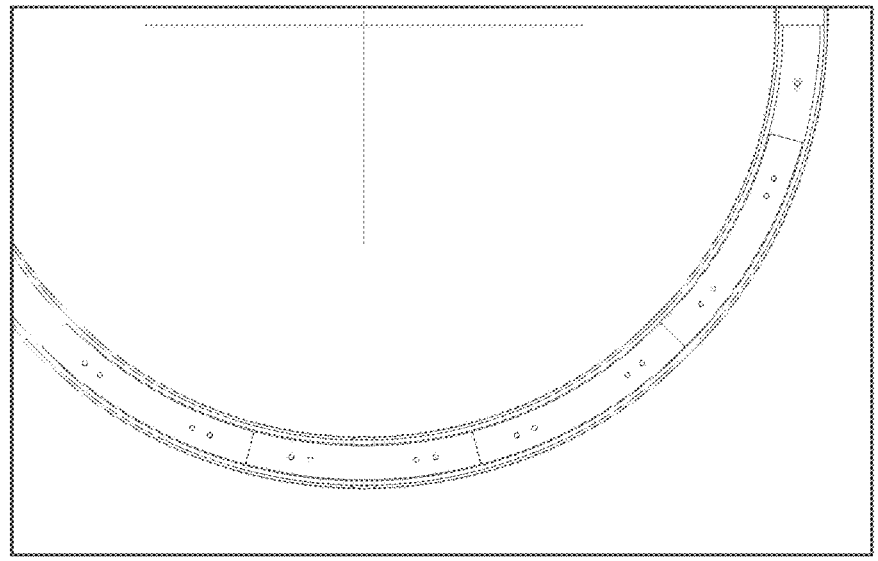

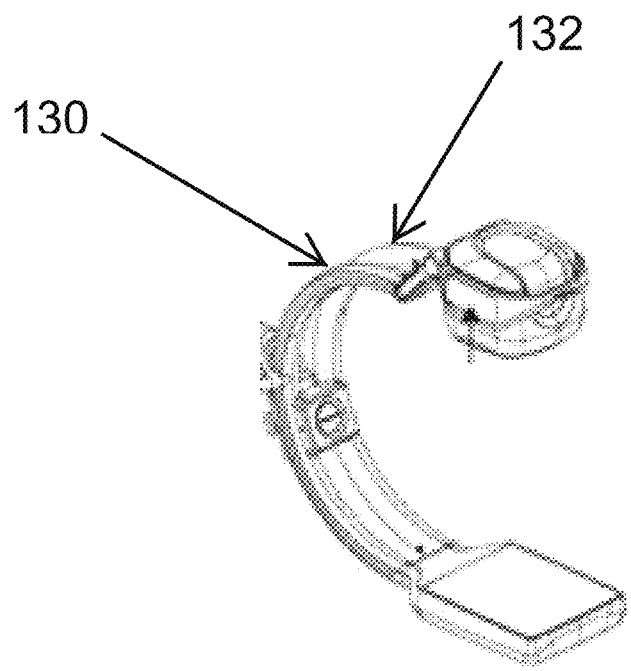
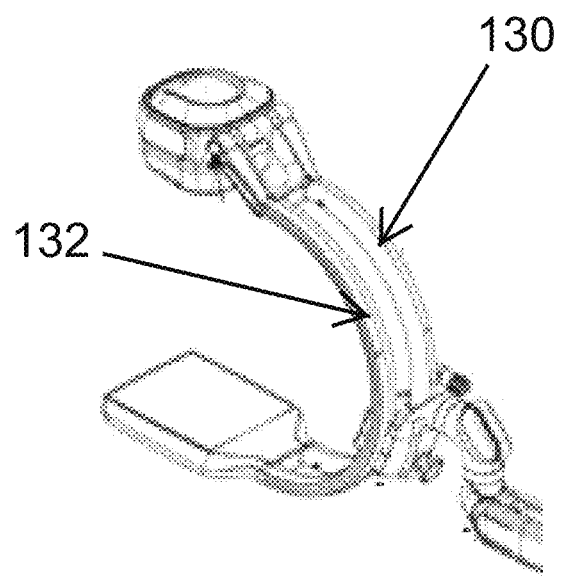
Fig. 21

FLUOROSCOPE WITH MOVABLE HEAD AND BARRIER TO VARY SOURCE TO SKIN DISTANCE

RELATED APPLICATIONS

The present application is a continuation-in-part of PCT/2018/037409 filed Jun. 13, 2018, which in turn claims the benefit of and priority to U.S. Provisional Application No. 62/519,707, filed Jun. 14, 2017, both of which are herein incorporated by reference in their entireties.

TECHNICAL FIELD

The subject technology relates to medical imaging devices and to fluoroscopy devices in particular.

BACKGROUND

Fluoroscopy is a means of producing real-time moving, continuous or static images of the interior structure of an object or person by using X-rays. The primary applications for such a device include medical imaging, non-destructive testing and various quality control applications. In this primary application, a physician may visualize the internal structure and organs, hard and soft tissues, blood flow analysis, cardiovascular processes, urological function and many other aspects of human anatomy. The advantages presented by using fluoroscopy in a medical capacity rests primarily in being able to observe human internal structures without the necessity to open the body for a direct or invasive procedure. Similarly, in non-destructive testing and quality control, aspects of structures, cables, components, physical properties and other characterizations can be made about an object without damaging the object in any material way.

The modern era of the fluoroscope began in 1940's with the Westinghouse Corporation inventing the first analog X-ray image intensifier. This allowed brighter pictures to be produced while producing less radiation in general. The repeatability and safety aspects of that invention led to the fluoroscope becoming a standard of care for surgical interventions in many situations/procedures. The ability to visualize the internal structures, organs and functions of the human body without necessarily cutting the patient open, or subjecting the patient or operator to unsafe doses of radiation led to safer, cleaner procedures with better outcomes.

That trend has continued up to the present with continual improvements to provide the fluoroscope operator and patient (user and subject) with higher quality diagnostic information with safer applications of radiation dosage while improving the outcomes of the procedure. Advancements in adjacent technologies have also fueled the continual innovation of the fluoroscope with the analog electronic era giving way to the digital electronic era to continue to push the advancement of these core principles: lower dose, higher quality data and better outcomes.

SUMMARY

The disclosed technology relates to a fluoroscope having an adjustable source to intensifier distance (SID). In one embodiment, to comply with safety regulations, a X-ray transparent spacer is positioned between the X-ray source and the intensifier. As the distance between the X-ray source and the intensifier is changed, the X-ray transparent spacer is moved or a different sized transparent spacer is used to ensure compliance with a minimum skin to source distance (SSD).

In one embodiment, a mechanical linkage moves the transparent spacer as the X-ray source is moved with respect to the intensifier. In yet another embodiment, sensors detect the SID and an electromechanical drive mechanism moves the X-ray transparent spacer to a correct distance from the X-ray source. In yet another embodiment, a processor provides an alert to an operator to use a correctly sized X-ray transparent spacer depending on the detected SID.

BRIEF DESCRIPTION OF THE DRAWINGS

FIG. 20 shows a number of weights that can be placed at different positions within a hollow C-rail to adjust a center of gravity in accordance with an embodiment of the disclosed technology.

FIG. 21 shows a C-arm with a pair of C-shaped rails that are held in a spaced parallel relation in accordance with an embodiment of the disclosed technology.

DETAILED DESCRIPTION

Figure 1:
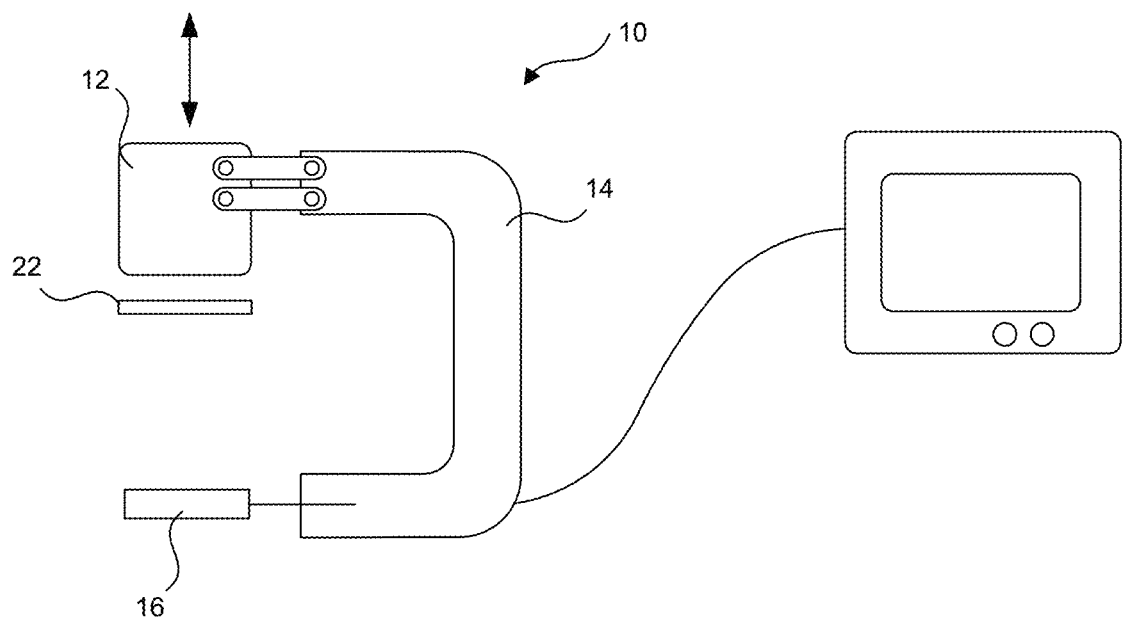
FIG. 1 illustrates a fluoroscope with an adjustable head to intensifier distance in accordance with one embodiment of the disclosed technology.

In the modern era, there are many manufacturers of fluoroscopes. Two primary categories of medical fluoroscope exist: fixed room devices and mobile fluoroscope devices. The fixed room devices are typically large, immobile devices installed in purpose-built specialty operating areas. Mobile fluoroscope devices are smaller and mobile. These units are typically moved from location to location to perform imaging tasks. The mobile fluoroscopic devices are also commonly referred to as "C-arms" due to the physical shape of the gantry holding the X-ray generator and the X-ray intensifier/detector on opposing ends, which is shaped in the lateral perspective at least somewhat like the letter "C".

The US Food and Drug Administration regulates C-arms largely as class II devices and provides regulations governing their manufacture and use in the United States. The relevant code sections may be found in 21 C.F.R. Parts 800-1299 and specifically in 21 C.F.R. § 1020.32 (Fluoroscopic Equipment). Within the FDA guidance and regulations provided, several small distinctions in size and characteristics of the C-arm can create different allowances or rules for operation. One of the primary distinctions lies in a geometric dimension referred to as "Source to Intensifier Distance" or (SID). The SID is the distance between the focal spot or origin point of the X-ray beam produced (where the X-rays are generated within the X-ray tube) and the Image Receptor or Intensifier that captures the resultant X-ray beam after passing through the patient or object under examination.

In 21 C.F.R. § 1020.32(g)(2), a distinction is made for a device having an SID less than 45 cm. This distinction leads to several specific guidelines and regulations for devices having an SID larger than 45 cm., commonly referred to as a "Full Size C-arm" and devices having an SID smaller than 45 cm. commonly referred to as a "Mini C-arm." This distinction leads to the advantages provided by the innovations contemplated in this application. The favorable guidelines allowed for the Mini C-arm in aspects such as source to skin distance and dosimetry testing compliance are preferable when imaging small anatomy. Typically, a Mini C-arm is used for "extremity use only" meaning shoulder to fingertip and knee to toe of the patient. The FDA requires a label advising the user of exactly that limitation. While this limitation allows for favorable design considerations, the geometry can be limiting to users who are addressing obese or large patients, or dealing with specific geometries of tables, apparatus and other objects interfering with positioning of the device near the patient.

The disclosed technology relates to a fluoroscope device that can operate under the favorable design guidelines and conditions of the Mini C-arm while being able to accommodate larger anatomy and specific surgical impediments. To that end, the following descriptions and embodiments outline such a solution that would allow the operator to choose the SID and allow the unit to operate as a Mini C-arm in a first configuration and to operate as a full size C-arm in an alternate configuration.

FIG. 1 shows one embodiment of a fluoroscope constructed in accordance with an embodiment of the disclosed technology. The fluoroscope 10 has an X-ray source 12 that secured to a supporting C-arm 14. The C-arm 14 also supports a X-ray receptor 16, which can include an X-ray image intensifier, flat panel X-ray detector or the like (referred to hereinafter as the receptor 16). Image data collected by the X-ray receptor 16 are gathered and processed in an image processor (not separately shown) and displayed on a monitor 20 for a physician or their assistant to view. In addition, the image data may be stored on a computer readable media or transmitted to a remote location for storage and analysis.

As discussed above, an operator of the fluoroscope 10 can change the distance between the X-ray source 12 and the X-ray receptor 16 in order to accommodate larger patients or to facilitate different imaging angles. In one embodiment, a linkage mechanism between the X-ray source 12 and the C-arm 14 allows the distance between the X-ray source 12 and the X-ray receptor 16 to be adjusted. As the distance is adjusted, an X-ray transparent spacer 22 is positioned between the X-ray source and the X-ray receptor 16 that prevents a patient's skin from coming any closer to the X-ray source than is permitted by the government safety regulations. In some embodiments, when the X-ray source to intensifier distance (SID) is greater or equal to 45 cm., the transparent spacer 22 is positioned so that a minimum source to skin distance (SSD) is 20 cm. or greater. When the X-ray source to receptor distance is less than 45 cm., the X-ray transparent spacer 22 is positioned so that the minimum source to skin distance is 10 cm. or greater. The transparent spacer 22 is made of an X-ray transparent material, such as plastic, and is positioned between the patient's skin and the X-ray source. In some embodiments, the transparent spacer 22 is automatically moved as the SID is changed. In other embodiments, an operator is prompted to change or move the transparent spacer 22 depending on the SID.

Figure 2:
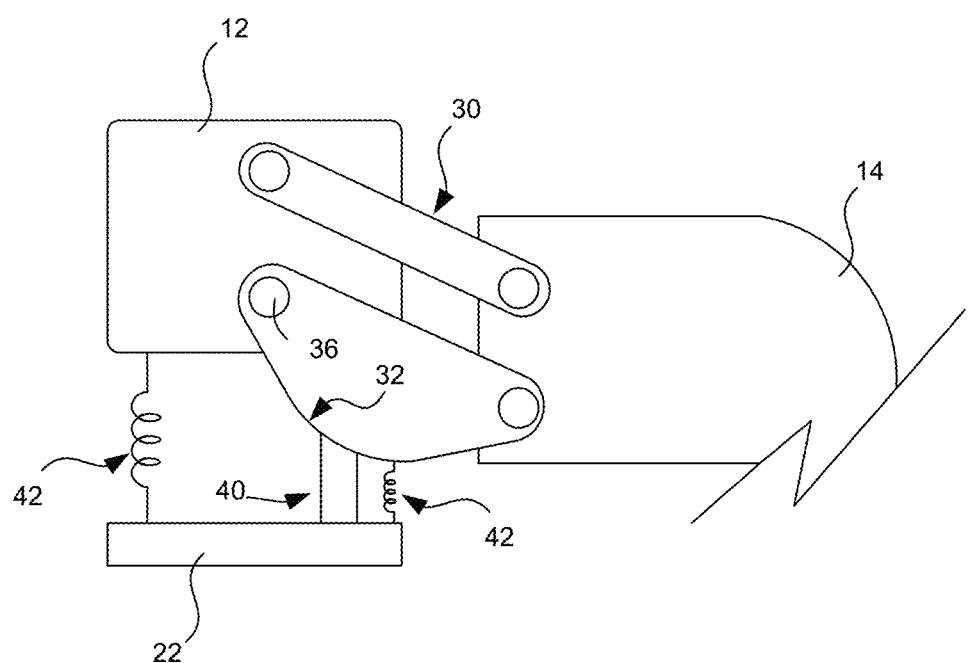
FIG. 2 illustrates a mechanism for maintaining a minimum source to skin (SSD) distance as a space between the X-ray source and the intensifier is changed in accordance with an embodiment of the disclosed technology.

FIG. 2 shows one embodiment of a mechanism for moving the transparent spacer 22 as the position of the X-ray source 12 is changed with respect to the receptor 16. In this embodiment, a parallel linkage 30 couples the X-ray source 12 to an end of the C-arm 14. The linkage 30 could have a friction fit so that it can be moved without loosening a locking mechanism or the linkage 30 may include such a locking mechanism to hold the X-ray source 12 at a desired position with respect to the C-arm 14. With the linkage 30, a user can move the X-ray source 12 either towards or away from the receptor 16.

In one embodiment, the linkage 30 includes a link with a convex-shaped lobe 32. The transparent spacer 22 includes a cam follower 40 that rides on the convex-shaped lobe 32. Springs or other tensioning devices 42 between the transparent spacer 22 and the X-ray source 12 hold the cam follower 40 onto the convex-shaped lobe 32. When the X-ray source 12 is moved downwards towards the receptor 16, the radius of the convex-shaped lobe 32 is sized so the distance between the X-ray source and the cam follower 40 decreases. As the X-ray source 12 is moved away from the receptor 16, the cam follower 40 follows an increasing radius of the convex-shaped lobe 32 to push the X-ray transparent spacer 22 away from the x-ray source 12, thereby increasing the SSD of the fluoroscope 10.

In addition to mechanical mechanisms for changing the SSD, it will be appreciated that electromechanical mechanisms could also be used. For example, the distance between the X-ray source 12 and the receptor 16 can be measured with an optical or acoustic distance measuring detector. Similarly, sensors or micro-switches on the linkage can also be used measure the rotational positions of the linkage members. Based on the measured or determined linkage position, a drive mechanism such as motor-driven screws or the like can operate to move the transparent spacer 22 towards or away from the X-ray source.

In some embodiments, the position of the transparent spacer 22 can be moved continuously and in other embodiments, the position of the transparent spacer can move in quantized amounts (e.g. 2 cm. changes, 5 cm. changes, etc.) as the distance between the X-ray source 12 and the receptor 16 changes. For example, an electromechanical movement can have defined stopping points or the radius of the convex-shaped lobe could be stepped instead of being continuously variable.

Figure 6:
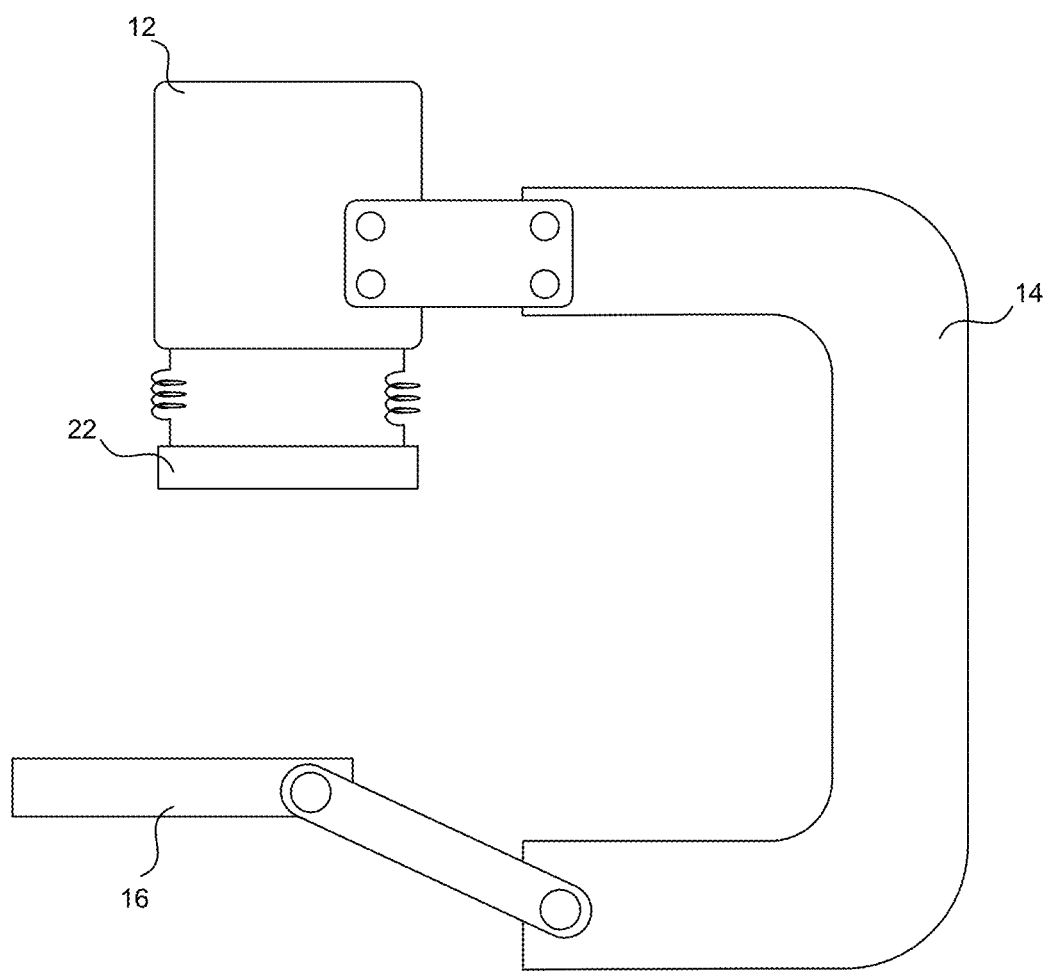
FIG. 6 shows a fluoroscope in accordance with another embodiment of the disclosed technology.

In some embodiments, the X-ray source 12 remains fixed with respect to the C-arm 14 and the receptor 16 is movable towards or away from the X-ray source as shown in FIG. 6. A detector (optical, acoustic, mechanical micro-switches or the like) determines the distance between the receptor 16 and the X-ray source 12 and the drive mechanism moves the X-ray transparent spacer 22 accordingly.

Figure 3:
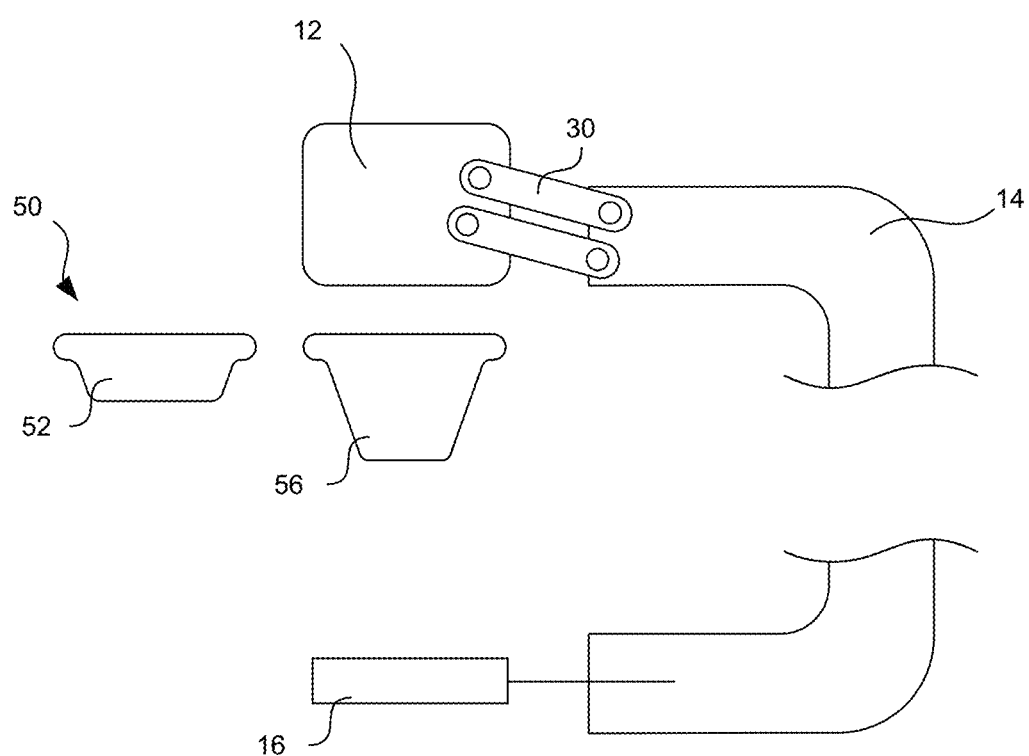
FIG. 3 illustrates a number of differently sized spacers that can be positioned between an X-ray ray source and an intensifier in accordance with an embodiment of the disclosed technology.

In some embodiments, different sized spacer cones 50 are inserted into a space between the X-ray source and the receptor 16. FIG. 3 shows a pair of spacer cones 52, 56. The spacer cones are solid or hollow and preferably made of an X-ray transparent material (e.g. plastic) and have height that is selected such that when a spacer cone is secured to the X-ray source, a body is prevented from coming within the minimum SSD determined for the particular source to intensifier distance. In other embodiments, the spacer cones 52, 56 can be formed as a frame or cage having a size that limits how close a patient's anatomy can get to the X-ray source in order to maintain the desired SSD. Such a frame can intercept a portion of the X-ray beam or can be designed such that the beam passes through an opening in the frame. Frames or cages of different sizes can be placed between the X-ray source and the receptor 16 depending on the measured SID and the desired SSD.

In some embodiments, the source to intensifier distance is measured or determined with a sensor and a controller displays a message on a display associated with the fluoroscope asking the operator to install the correctly sized spacer cone. In some embodiments, the spacer cones fit with a receptacle slot on the X-ray source and can be mechanically, optically or electrically encoded so that a controller can confirm that the correct spacer cone is installed before X-rays are produced.

As indicated above, in a smaller configuration such as a Mini C-arm, the device would be allowed a minimum source to skin distance of 10 cm with an optional 10 cm spacer provided. In a full-size configuration, the source to skin distance is selected to be a minimum of 20 cm. with an optional 10 cm. spacer cone. Allowing the SID to change from a size that is less than 45 cm. to a size greater than 45 cm. but retain the properties of both Mini C-arm and Full Size C-arm when in use provides a great advantage in terms of radiation safety and physical configuration. The lower radiation dose applied by a Mini C-arm coupled with the larger area to operate would certainly be desirable to the operator and consumer in terms of safety and clinical outcome.

A corresponding requirement to this advantageous SID change would be a means of changing the minimum source to skin distance (SSD) mandated by 21 C.F.R. Being able to change the SSD either independently or in concert with the SID presents distinct advantages. This motion could be mechanical, electromechanical, synchronized with SID or not synchronized with SID.

In alternate embodiments, the X-ray assembly by itself could be moved further from the image receptor, or the image receptor could be moved further away from the X-ray assembly, or a combination of the two motions could achieve the same change in SID.

The mechanism of motion of the X-ray source or the receptor to modify the SID could be linear, curved, orthogonal, achieved with linkage, drives, belts, gears, screws, springs, dampers, and many other conceivable mechanisms. The control can be electronically powered or mechanically controlled. Motorized or manual, the movement affects the same outcome of the advantage of the variable SID.

The spacing of the source to skin distance could also be accomplished in any number of ways. The floor of the surface closest to the image receptor could be made to move to increase or decrease the SSD as desired. If this adjustment is made mechanically it could simply be made electronically as well.

The SSD adjustment could be accomplished by a mechanical or an electronic linkage to the SID adjustment mechanism in concert or at least in a coordinated fashion.

The same could be accomplished by using a series of spacers of varying thicknesses either alone or in combination to create different desirable SSDs. Such spacers could be mechanically or electrically placed between the X-ray source and the intensifier as required.

The limits of travel for both the SID adjustment means as well as the SSD adjustment means could be tracked and monitored by micro-switches, potentiometers, mechanical gauges, or other means to allow the system to register the current configuration of the components e.g. which position the X-ray source is in relative to the image intensifier and what the position the SSD spacing mechanism is relative to the X-ray source.

Figure 4B:
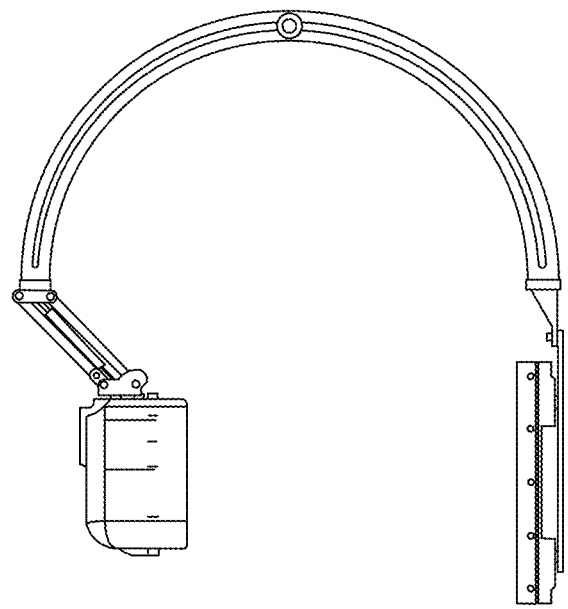
FIGS. 4a and 4b show another embodiment of a fluoroscope in accordance with some embodiments of the disclosed technology.
Figure 4A:
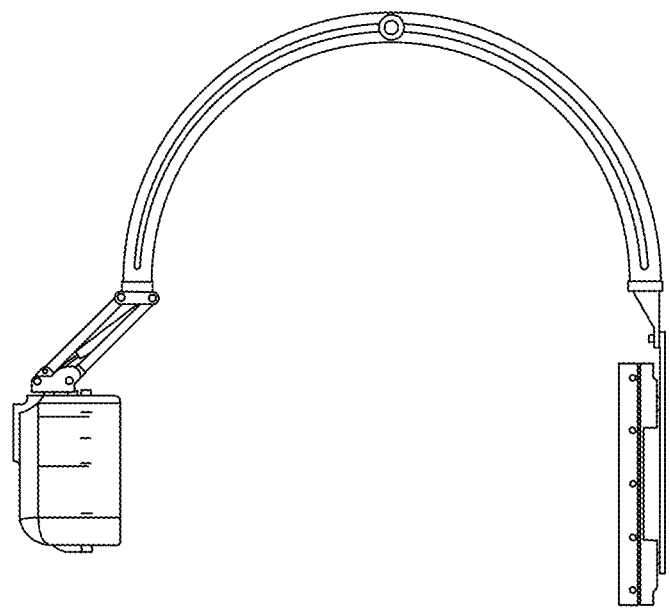

FIGS. 4*a* and 4*b* show an X-ray source that is made to vary in distance from the receptor to a size less than 45 cm (SID minimal position) and greater than 45 cm (SID Maximal Position). The embodiment in FIGS. 4-*a*—and 4-*b*—shows a device that would align to two preferred heights and operate only in those two designed positions. The linkage could be designed to allow different ranges and means of motion to allow for more than two preferred positions, to infinite stepless operable selections between the maximum and minimum range. (Such as with a manual linear rack, or motorized rack or other means.)

Figure 5:
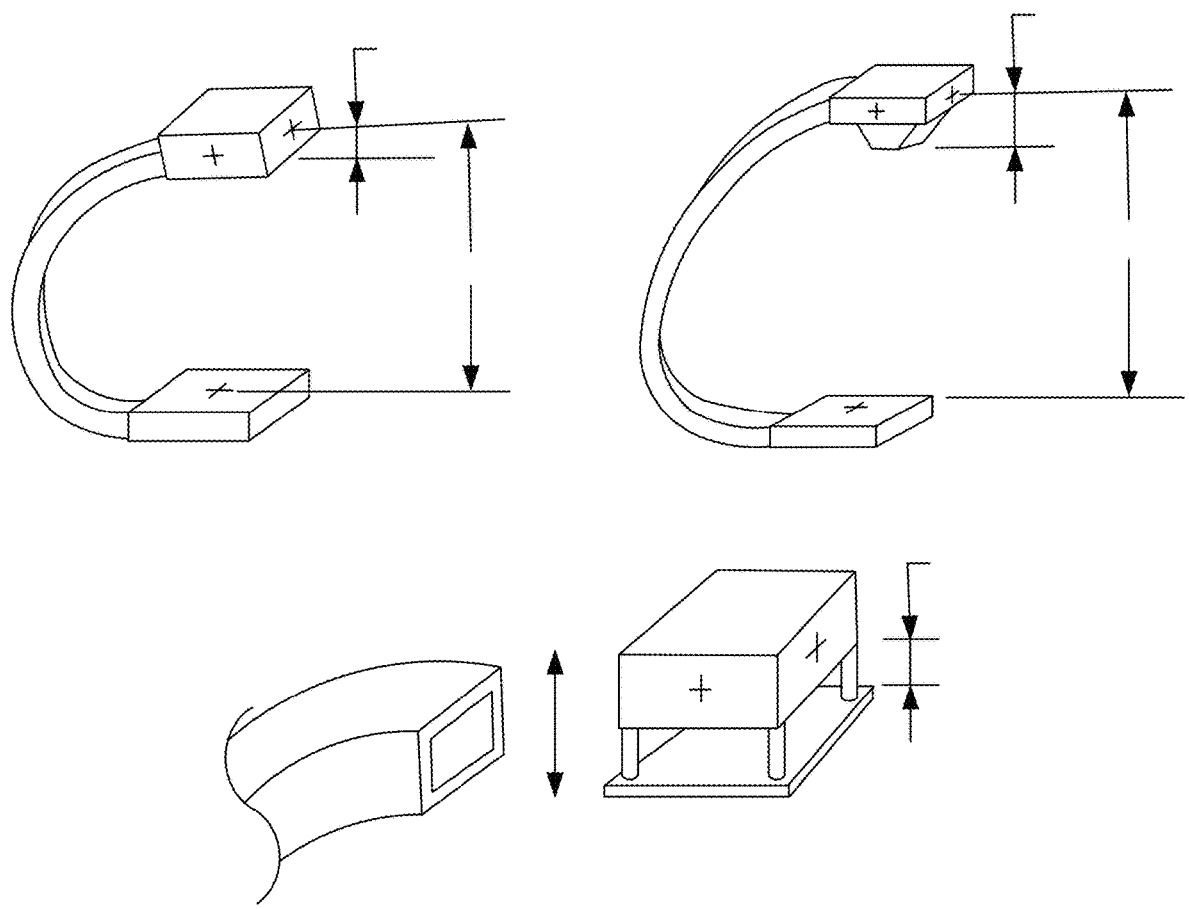
FIG. 5 shows a fluoroscope in accordance with some embodiments of the disclosed technology.
Figure 7:
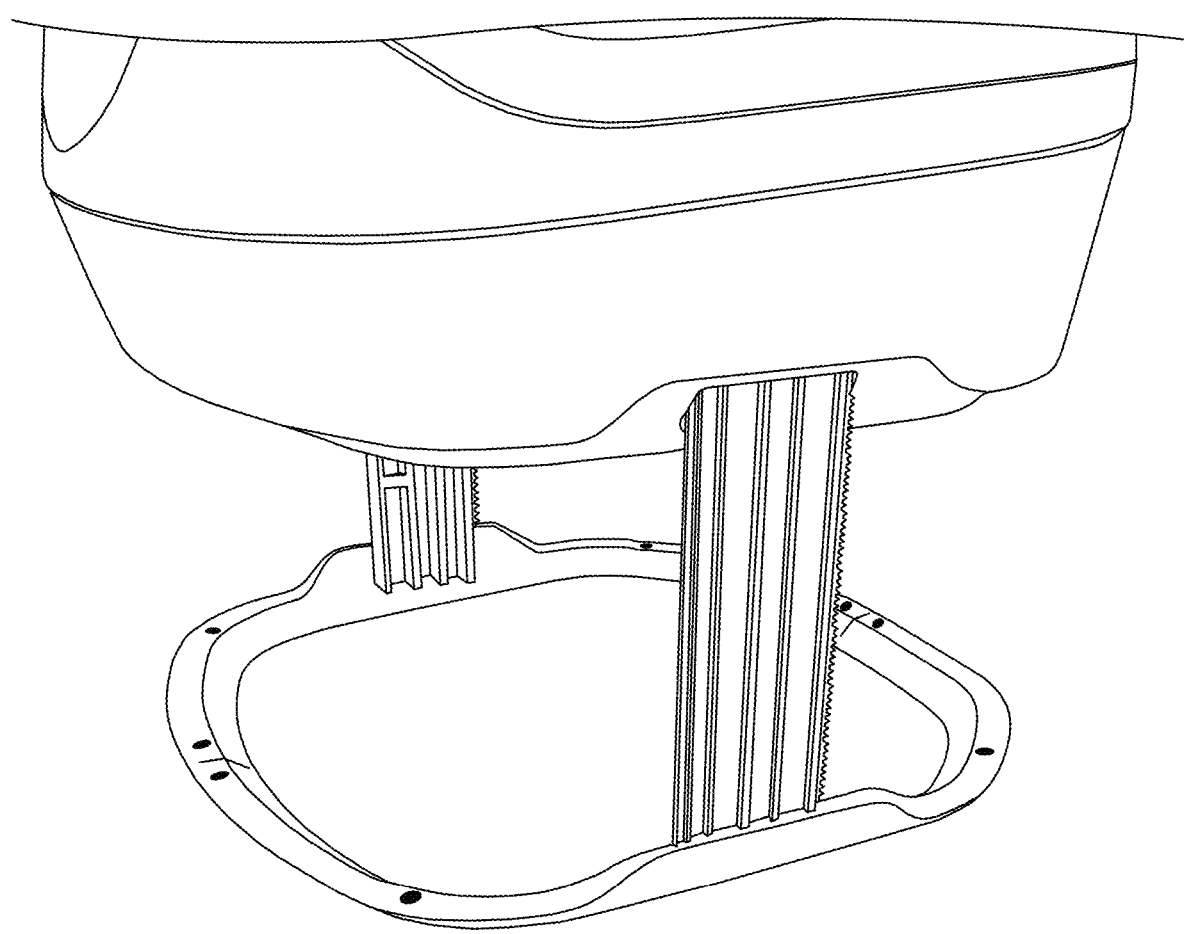
FIG. 7 shows a frame for maintaining a minimum SSD in accordance with an embodiment of the disclosed technology.

FIG. 5 shows a sketch of a fluoroscope having a variable SSD in accordance with some embodiments of the disclosed technology. A variable SID would be valuable for accommodating patients and users in more scenarios. Obeying both criteria could be accomplished by providing a variable SID that has an accompanying means of expanding the SSD as well. The source or receptor could move relative to each other to vary the SID. As shown, a source includes an adjustable mounting height on the end of the C-arm. A radiotranslucent barrier (or an open frame as shown in FIG. 7 with a hole to pass X-rays and a frame body to prevent contact with the source) holds the SSD at a desired distance. The SSD can be changed by moving the barrier closer or further from the source. Pegs or worm gear posts can lift or lower the SSD barrier relative to the source. A microswitch can enable/disable X-rays if the barrier is in the wrong position. In the embodiment shown in FIG. 5, the X-ray tube is positioned 10 cm from the bottom surface of the imaging head so that when the SID is greater than 45 cm. an extra 10 cm. spacer is required by the governmental regulations. In the Mini C-arm configuration, no additional spacer is required. The spacer could be manually inserted or mechanically or electromechanically driven.

Figure 8:
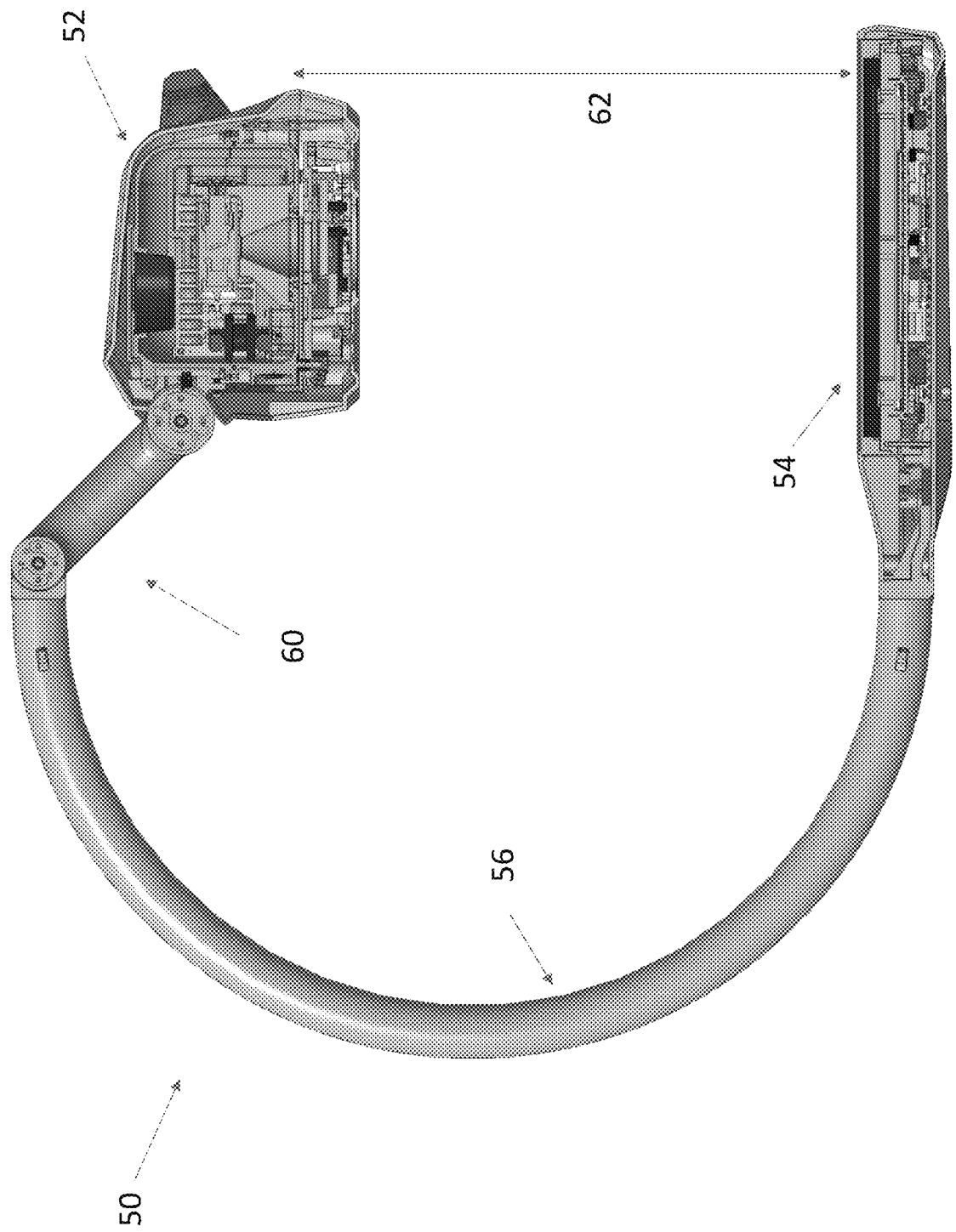
FIG. 8 shows a fluoroscope with a movable imaging head including an X-ray source in a down or Mini C-arm position in accordance with an embodiment of the disclosed technology.
Figure 11:
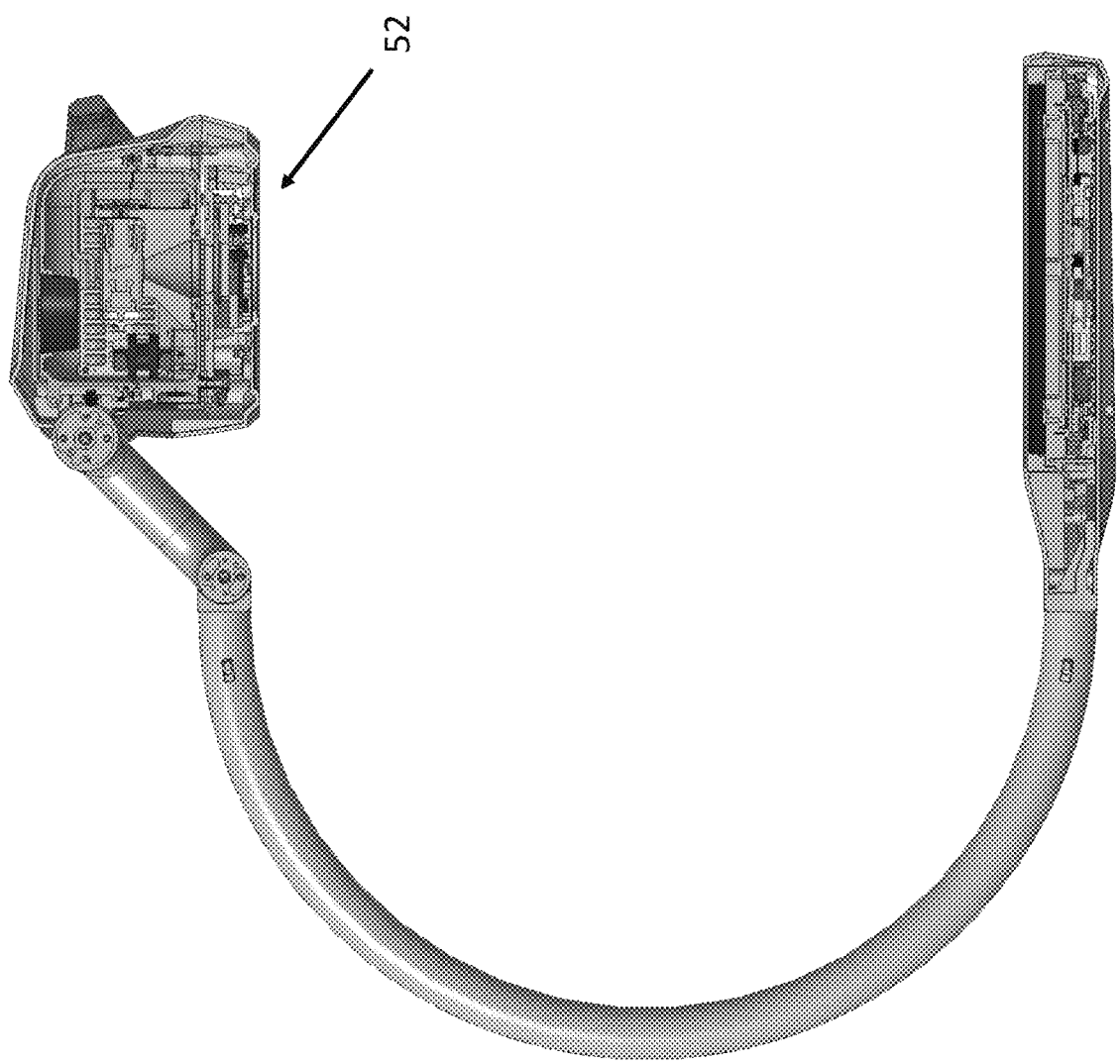
FIG. 11 shows a fluoroscope with a movable imaging head in a full size C-arm position in accordance with an embodiment of the disclosed technology.

FIG. 8 shows a portion of a fluoroscope 50 that is movable between a full size C-arm configuration and a Mini C-arm configuration in accordance with one embodiment of the disclosed technology. The fluoroscope 50 includes an imaging head 52 (including an X-ray source) that is movably mounted on one end of a pair of circular rails 56 with a four bar linkage (partially shown) and an X-ray receptor 54 that is mounted on the other end of the circular rails 56. The imaging head 52 is movable towards and away from the X-ray receptor 54 to convert the fluoroscope 50 between a full size C-arm configuration and a Mini C-arm configuration. In the embodiment shown, the X-ray source is positioned 10 cm. above a bottom surface of the imaging head 52 so that when the fluoroscope is in the Mini C-arm configuration (e.g. SID<=45 cm.) as shown, the minimum SSD distance of 10 cm is maintained without the use of an additional spacer. When the imaging head 52 is raised to a full size C-arm configuration (see FIG. 11), the SID 62 is greater than or equal to 45 cm. and an additional spacer is placed in between the imaging head 52 and the X-ray receptor 54 to prevent tissue from coming closer to the X-ray source than is allowed. In one embodiment, the spacer is the type shown in FIG. 7 comprising a plastic barrier ring with a hole through the center that is extended from or retracted into the imaging head 52 depending on whether the fluoroscope is in the full size C-arm configuration or the Mini C-arm configuration.

Figure 9:
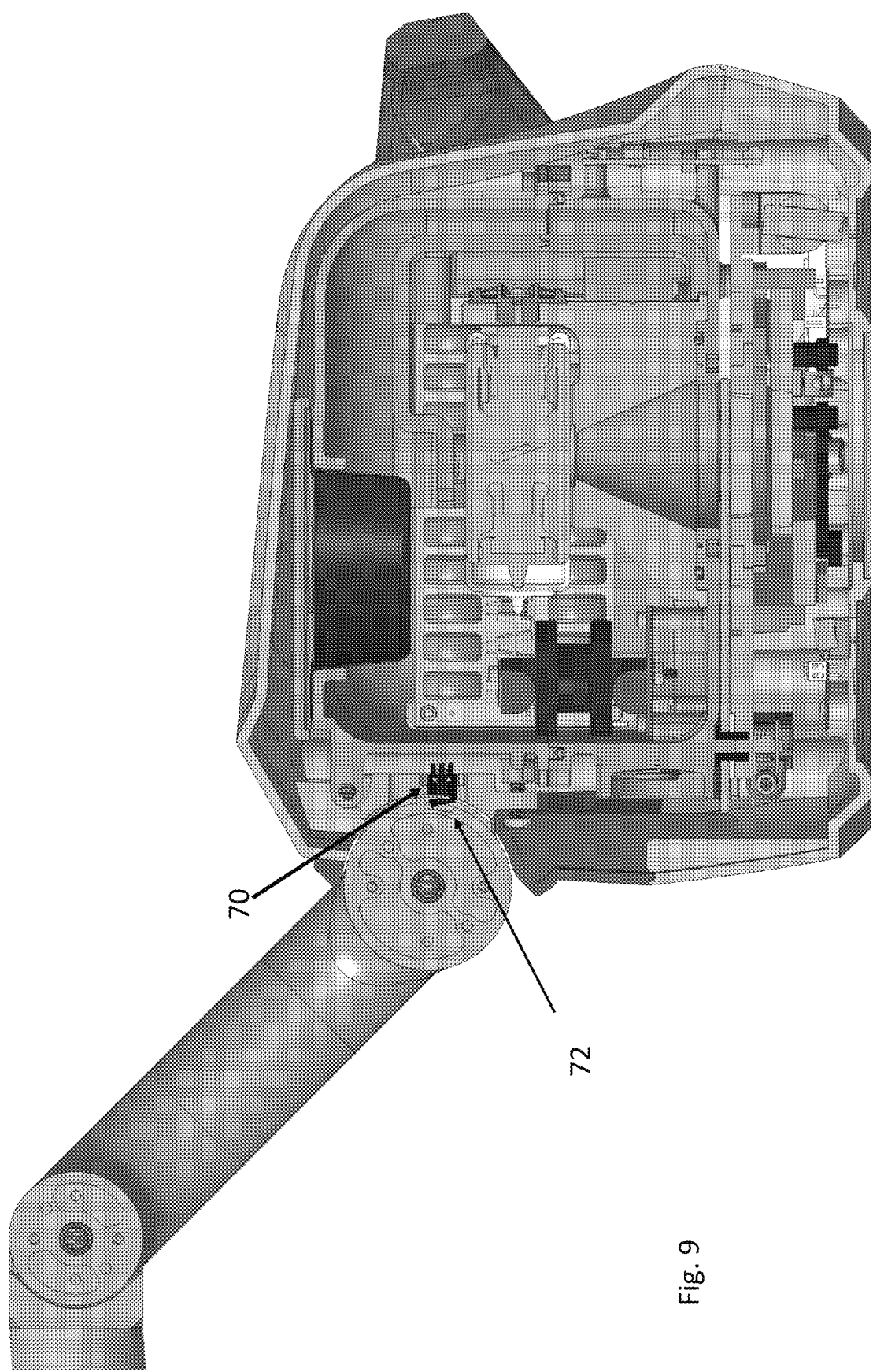
FIG. 9 is a cross-sectional view of the imaging head in the Mini C-arm position and a first micro-switch used to detect the position of the imaging head in accordance with an embodiment of the disclosed technology.
Figure 10:
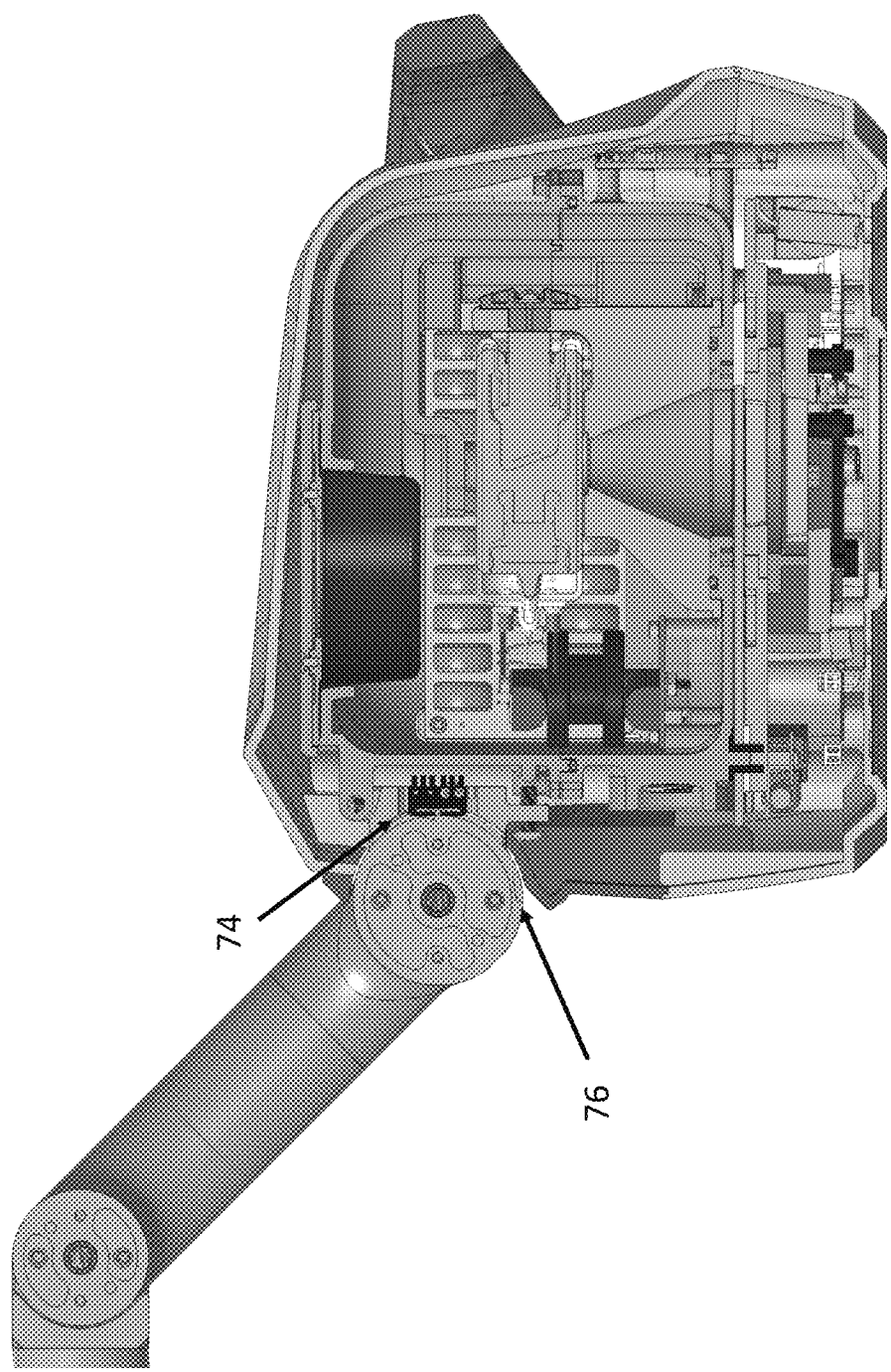
FIG. 10 is a cross-sectional view of the imaging head in the Mini C-arm position and a second micro-switch used to detect the position of the imaging head in accordance with an embodiment of the disclosed technology.

FIGS. 9 and 10 are two cross-sectional views taken at different depths in the imaging head 52 that show a pair of micro-switches in contact with the linkage mechanism that allows the imaging head to move. One of the micro-switches is configured to close when the imaging head 52 is positioned in the fully up position (e.g. full size C-arm) and the other of the micro-switches is configured to close when the imaging head 52 is in the fully down position (e.g. Mini C-arm). In one embodiment, the linkage mechanism includes a depression or recess on a hinge portion of the linkage. A micro-switch 70 has a contact that rides against the hinge until the contact drops into the recess 72 thereby opening the switch when the imaging head is in the Mini C-arm configuration. FIG. 10 shows an adjacent micro-switch 74 that is in the closed position when the imaging head 52 is in the Mini C-arm configuration. The notch or depression 74 is positioned on the surface of the hinge so that the micro-switch 74 will open when the imaging head is in the raised position (e.g. full size C-arm configuration).

Figure 12:
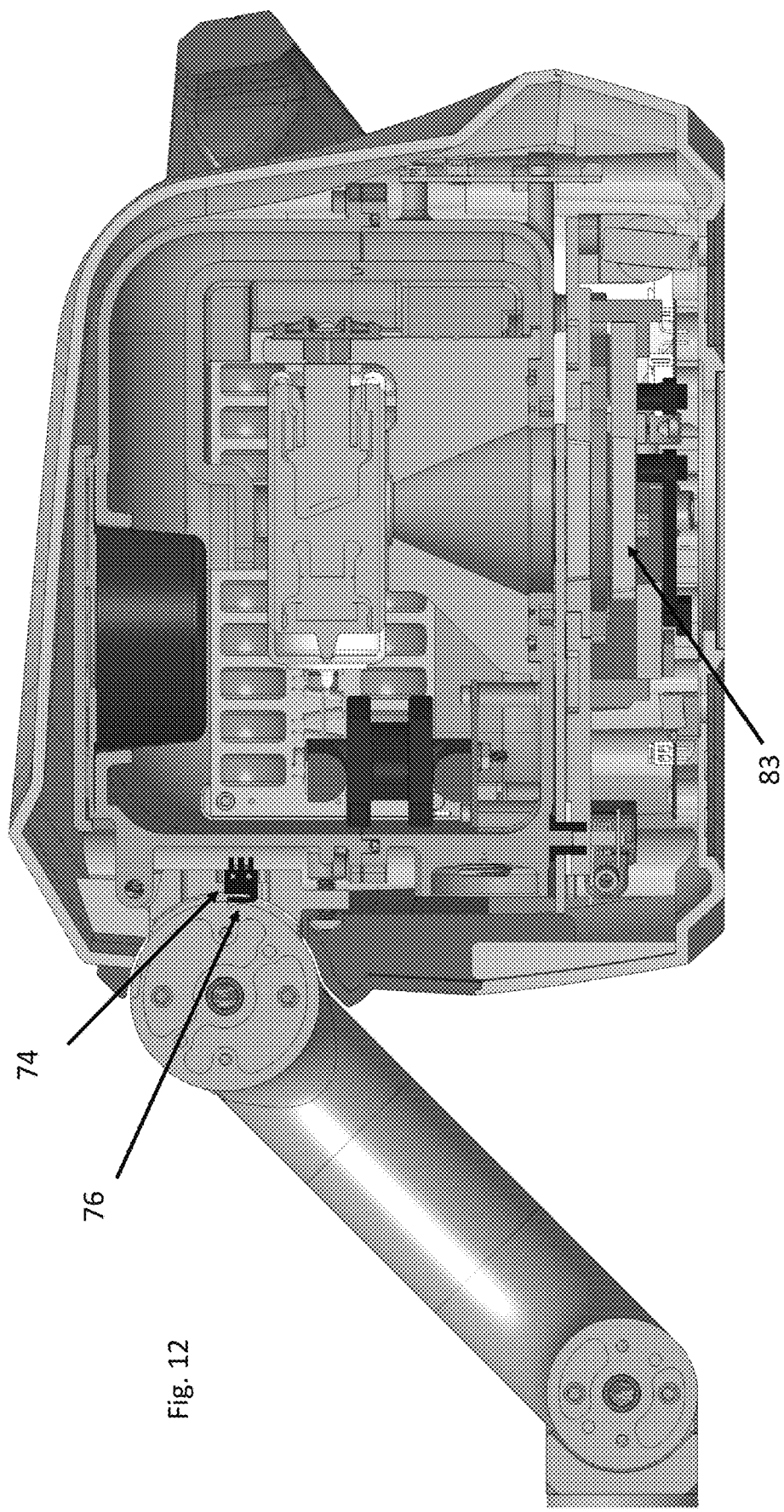
FIG. 12 is a cross-sectional view of the imaging head in the full size C-arm position as detected by the first micro-switch in a closed position in accordance with an embodiment of the disclosed technology.

FIG. 12 illustrates the position of the micro-switch 74 when the imaging head 52 is in the raised position (full size C-arm). Here, the contact of the switch 74 drops into the recess 76 on the hinge and the switch 74 opens.

As will be appreciated, instead of a recess in the hinge, the outer surface of the hinge could also include a slot in which the contact of the micro-switch rides and a ramp provided at the correct location on the hinge surface that closes the switch when imaging head is in a particular position.

In one embodiment, a computer system controlling the fluoroscope detects whether the system is in the full size C-arm configuration or the Mini C-arm configuration. If the system is in the full size C-arm configuration, the computer actuates a drive mechanism (e.g. servo motors, worm gears etc.) to extend or retract a spacer of the type shown in FIG. 7. In one embodiment, the computer actuates the drive mechanism to extend the spacer upon detection from a micro-switch that the imaging head is in the fully raised position.

Figure 13:
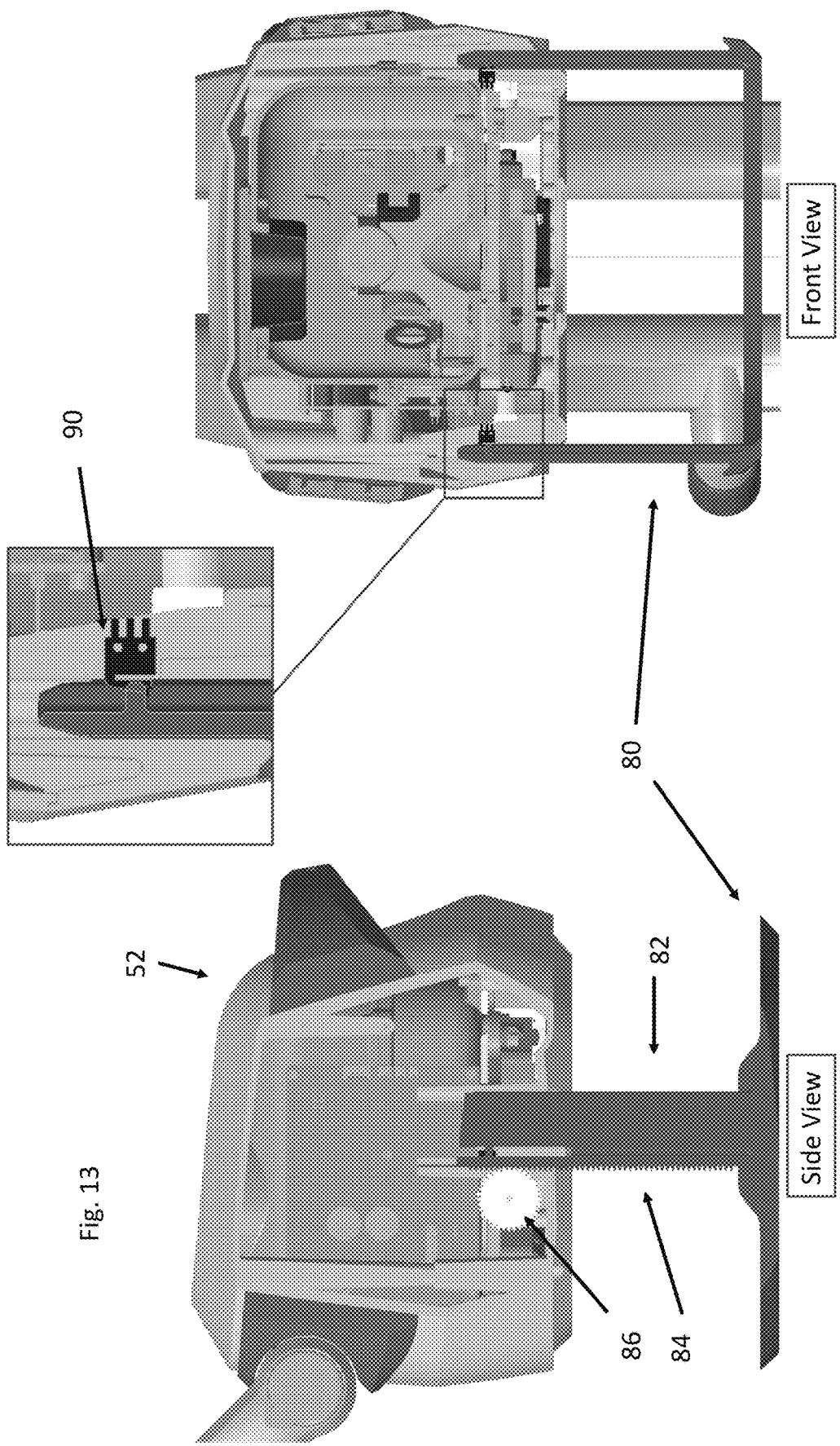
FIG. 13 shows a spacer in an extended position in accordance with one embodiment of the disclosed technology.
Figure 14:
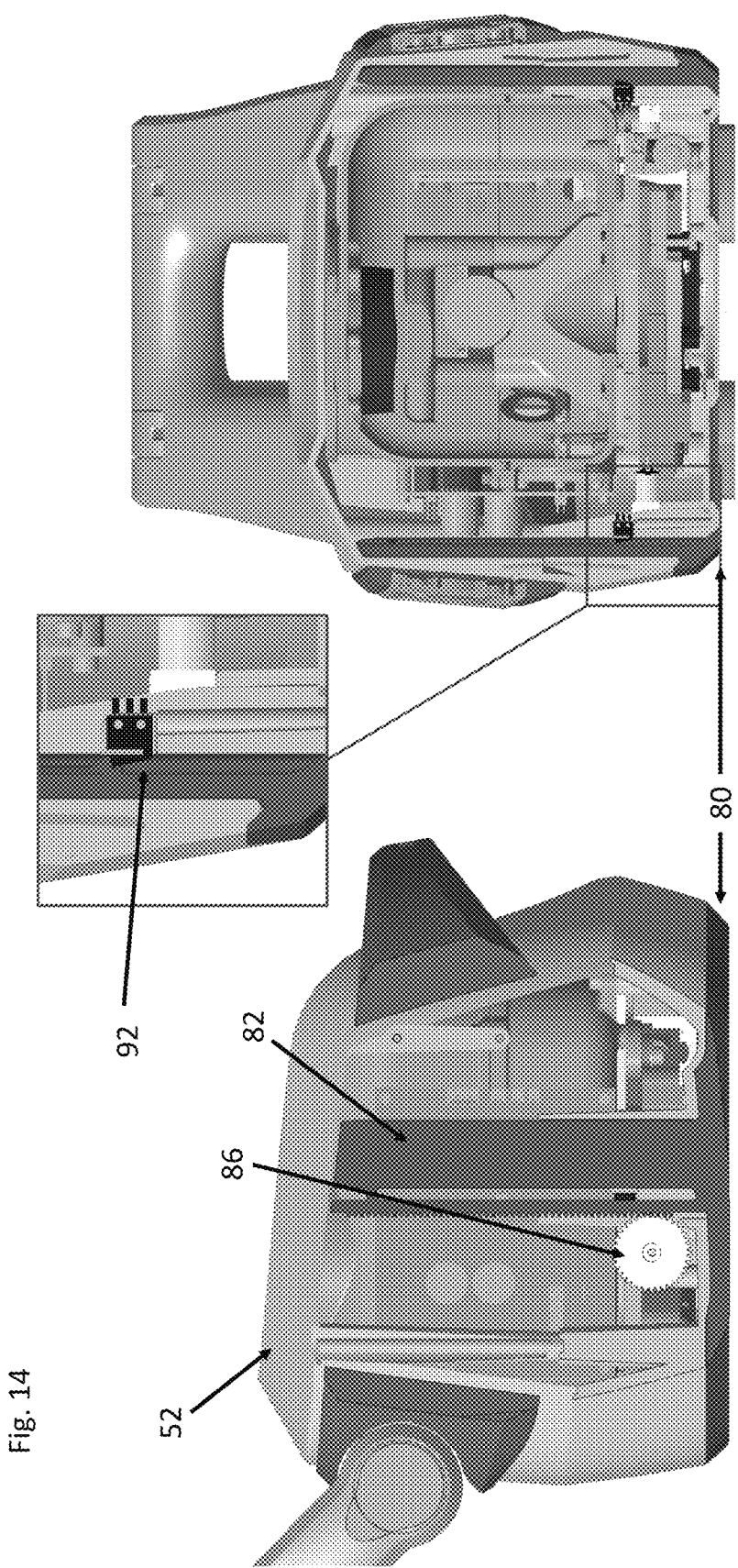
FIG. 14 shows the spacer in a retracted position in accordance with one embodiment of the disclosed technology.

FIGS. 13 and 14 show additional details of a spacer that can be extended or retracted in the imaging head depending on the configuration of the fluoroscope. In the embodiment shown, the spacer 80 is a ring of radiotranslucent material (e.g. plastic) having a hole in the center through which X-rays can pass (see FIG. 7). A pair of vertically extending arms 82 extend from the ring and into the body of the imaging head. Teeth 84 on at least one of the arms 82 mesh with a gear 86 that is driven by a motor to extend and retract the spacer 80. In one embodiment, a micro-switch 90 has a contact that engages a tab on an arm 82 when the spacer is in the fully extended position.

In the embodiment shown in FIG. 14, a contact of a micro-switch 92 is closed by a tab on an arm 82 of the spacer when the spacer 80 is fully retracted.

In some embodiments, the motor(s) that extend and retract the spacer 80 also produce a signal when the spacer is moved manually so that if the spacer is bumped or pushed closed or pulled open by a physician or an assistant, a computer system can drive the one or more motors to retract or extend the spacer.

As will be appreciated, the disclosed technology is not limited to the use of micro-switches to detect the position of the imaging head 52 with respect to the X-ray receptor and the position of the spacer. Other sensors (optical encoders, electronic encoders, acoustic sensors, IR sensors, position sensors or accelerometers and the like) could be used to determine if the imaging head is in the fully up or fully down position or some position in between. Similarly, if the spacer is of the type that is inserted into the imaging head, other types of sensors besides micro-switches such as magnetic reed switches, Hall effect switches, optical encoders etc. can be used to determine if the correct spacer is in place.

Figure 15:
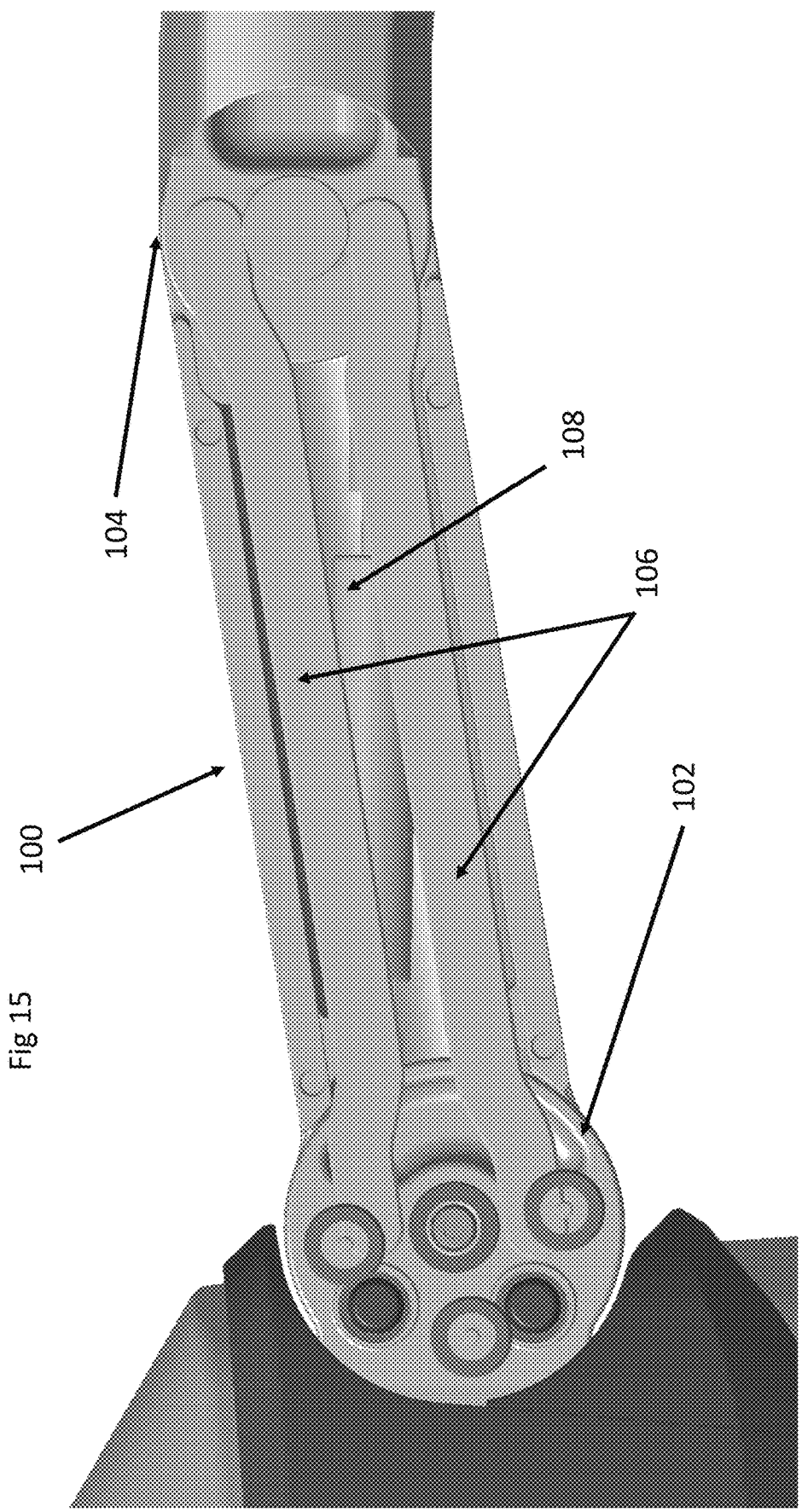
FIGS. 15-17 are various views of a four-bar linkage assembly used in accordance with one embodiment of the disclosed technology.
Figure 16:
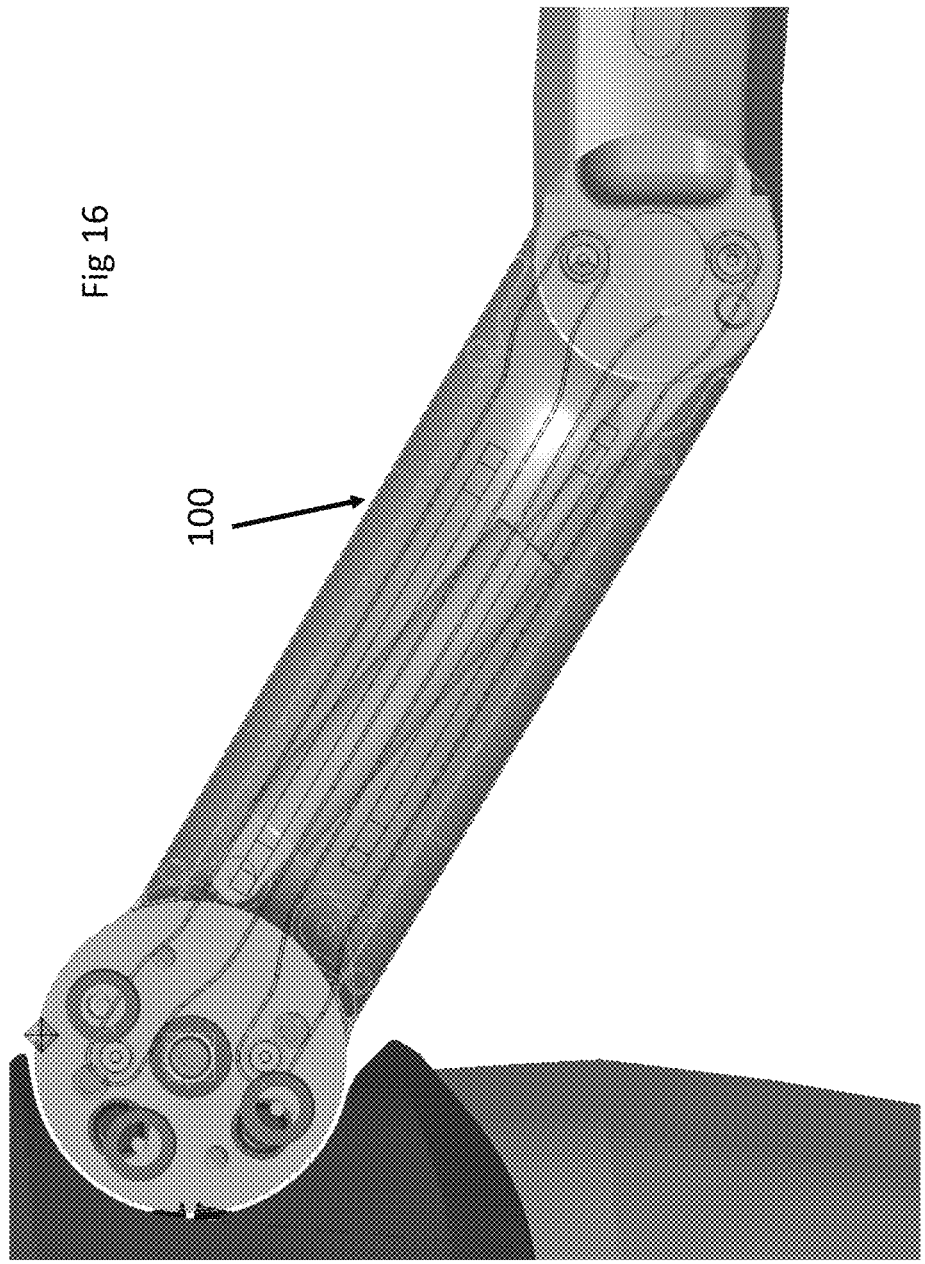
Figure 17:
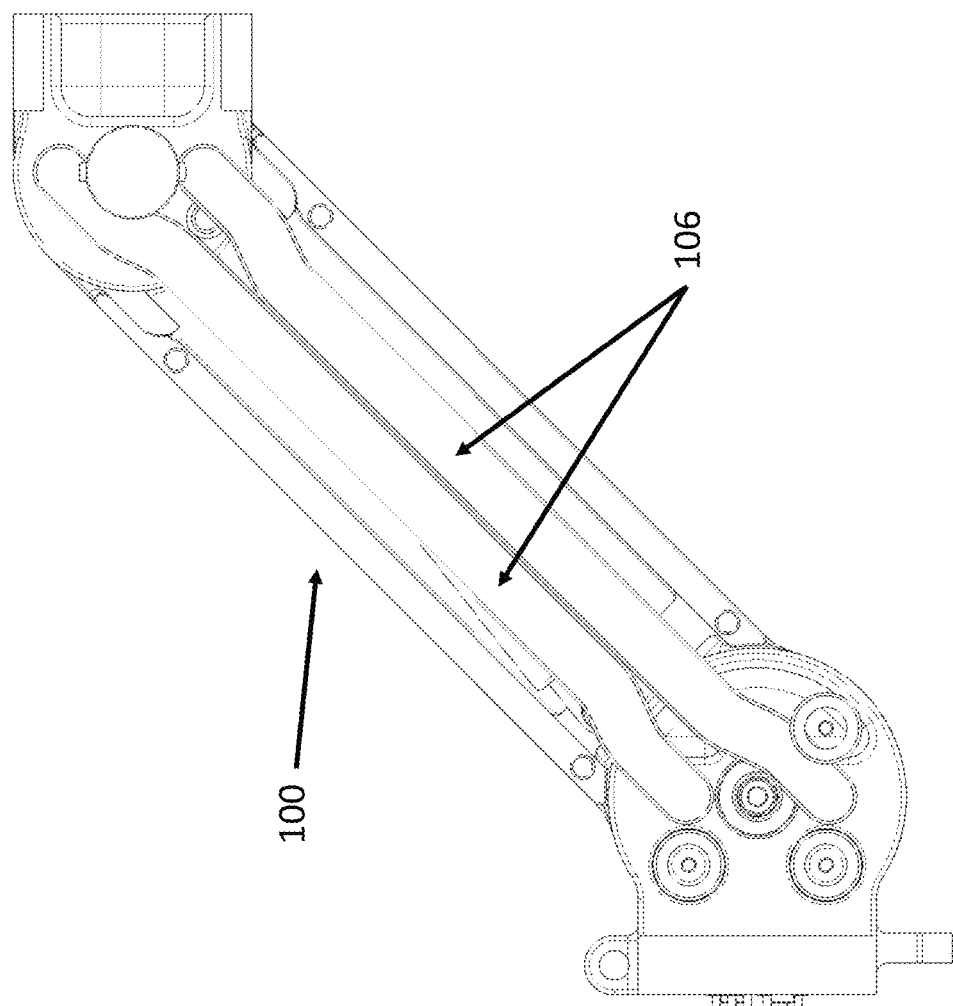

FIGS. 15-17 show one embodiment of a 4-bar linkage that connects the imaging head to the C-arm of the fluoroscope. The linkage includes two rotating hinge portions 102, 104 that are joined on either side of the linkage by two sets of linkage bars 106. The linkage bars 106 operate to tilt the imaging head as the imaging head is moved up and down so that it remains perpendicular to the X-ray receptor in both the full size C-arm and Mini C-arm position. A gas shock 108 is positioned in the linkage to maintain the position of the hinges when the linkage not being moved by an operator.

Figure 18:
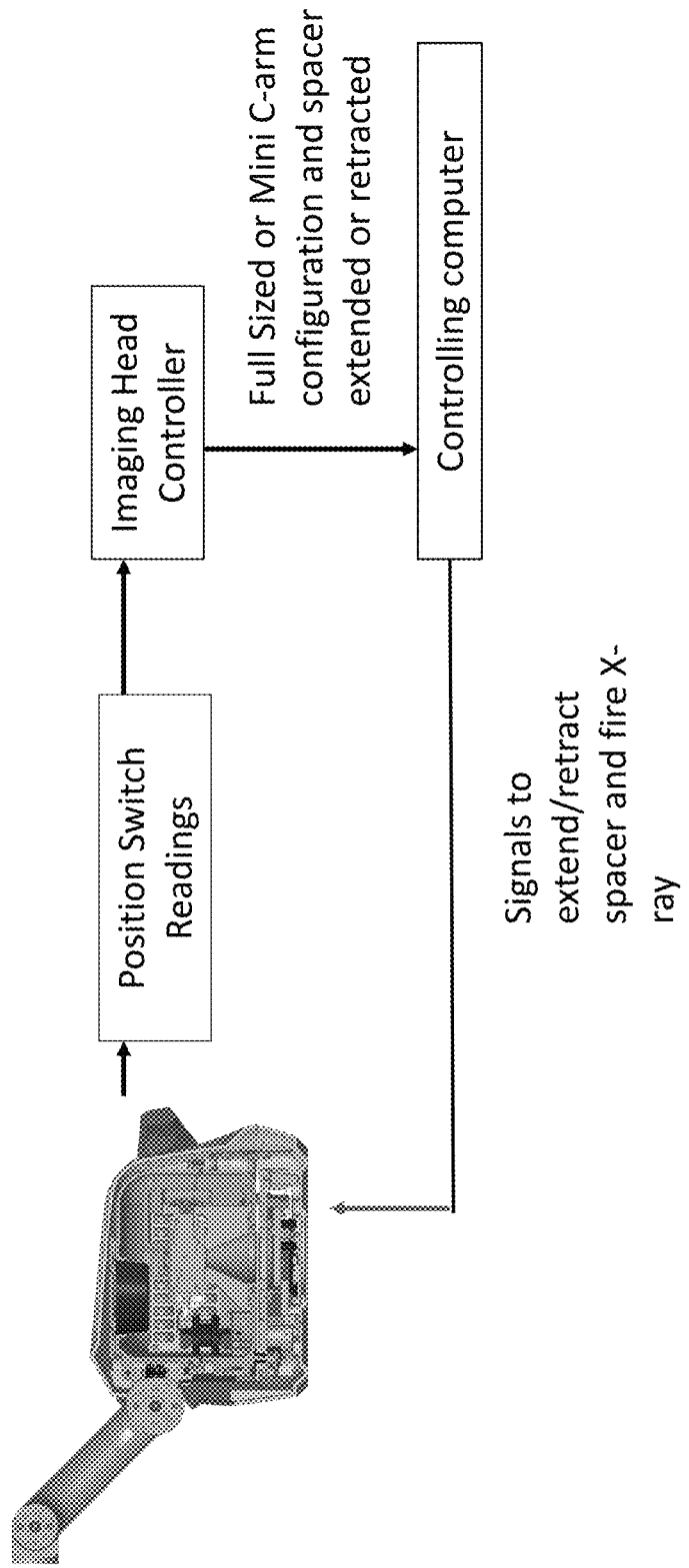
FIG. 18 is a block diagram of a computer system for controlling a fluoroscope in accordance with an embodiment of the disclosed technology.

In one embodiment as shown in FIG. 18, the micro-switches (or other sensors) produce output signals that are connected a controller (microcontroller, ARM processor or the like) in the imaging head 52 that is programmed to read the status of the switches or sensors and report the configuration of the system and whether the spacer is extended or retracted or in place to a controlling computer system. In one embodiment, the computer system is programmed to only allow operation when one micro-switch that detects the position of the imaging head is open and the other micro-switch that detects the position of the imaging head is closed (e.g. the imaging head is in the fully up or down position) and the spacer is in the correct position. Other states where both switches that detect the position of the imaging head are closed (e.g. at an intermediate position of the imaging head) cause the computer system to prohibit firing the X-ray source. Similarly, if both switches that detect the position of the imaging head are open (e.g. possible switch malfunction), the computer system also prohibits the X-ray source from firing. Similarly, the computer system is programmed to prevent firing the X-ray if the spacer is not in the correct position (e.g. extended for the full size C-arm configuration).

In some embodiments, the computer system is programmed to be overridden by a physician or X-ray technician so that X-rays can be generated even if the imaging head or spacer is not in the correct position if the physician deems that it is in the best interest of the patient or is required to perform a procedure.

Figure 19:
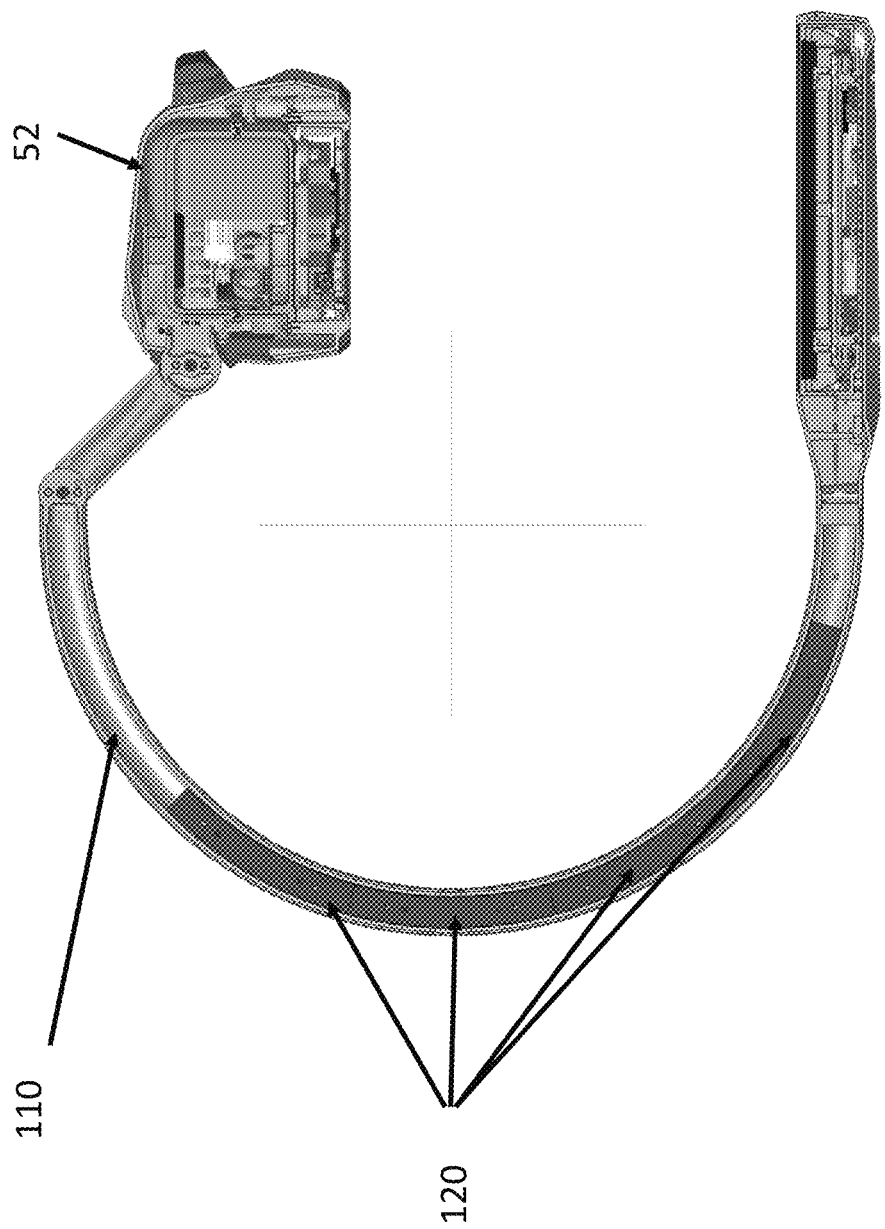
FIG. 19 shows a hollow C-rail in accordance with an embodiment of the disclosed technology.

In some embodiments, the fluoroscope can be built with X-ray receptors that may vary in size. Because different components can affect the balance of the C-arm, one embodiment of the disclosed technology employs a C-arm that includes a pair of laterally spaced cylindrical metal rails where the rails are a fully or partially hollow. A portion of the outer surface of the rails are removed to provide access to the hollow sections. As shown in FIG. 19, a C-arm includes a hollow semi-circular curved rail 110. Curved weights 120 can be secured at different positions within the hollow portion of the C-arm rail so that the center of gravity of the C-arm remains close to the center of the circle defined by the radius of the C-arm. In some embodiments, some portion of the C-arm rail is a solid curved cylinder and only a portion of the C-arm rail is hollow. Weights can be placed at two more locations within the hollow section(s). In other embodiments, the entire C-arm rail is hollow and weights can be placed at a number of different positions in the C-arm as shown in FIG. 20. The weights can be secured with bolts or the like to the wall of the hollow C-arm. A cover can be placed over the weights to complete the C-arm.

In some embodiments, the C-arm includes a pair of laterally separated, fully or partially hollow cylindrical rails 130, 132 as shown in FIG. 21. The rails are secured by welding or with bolts etc. to a pair of transverse spacer bars at their ends to maintain the parallel spacing between the rails. Although other configurations of the rails are possible. However, having a space between the rails can be useful to allow a physician to pass a tool or their hand between the rails for accessing the patient in difficult positions. In some embodiments, the rails may not include any hollow portions and a pair of solid rails that are weighted for a particular imaging head and imaging receptor could be used. A roller clamp includes four of more wheels (not shown) that ride on the outside and the inside of the C-arm rails. The wheels on the inside of the C-arms are drawn to the wheels on the outside of the C-arms (or vice versa) to lock the C-arms in the roller clamp. When the tension on the wheels is released, the C-arms can be rotated in the clamp. With the C-arm properly balanced, the C-arm will be less likely to rotate by itself and is easier to move.

In some embodiments, a patient's anatomy is secured to a support platform (not shown) disposed between the X-ray source and the intensifier. As shown in FIG. 6, the distance from the X-ray source to the support platform can be used as a proxy for the SSD if the anatomy is secured to the platform so that it cannot move closer to the X-ray source during operation of the fluoroscope. In this embodiment, the distance that the support platform can move towards the X-ray source is controlled based on the SID so that the anatomy cannot be positioned closer to the X-ray source that is allowed by safety regulations assuming an average anatomy size (e.g., 5-8 cm. in thickness). The position of the support structure towards or away from the X-ray source can be controlled with mechanical or electromechanical actuators, servo motors, gears or the like.

In any of the embodiments described, it is advantageous to provide a sterile barrier that accommodates both the smaller and larger SSD as well as any mechanical movements utilized in achieving the variable SID. As such, one embodiment may be a plastic sheeting or sheath covering the portions of the unit that would require sterility in operation. The sterile barrier could be designed with an integral or fitted elastomeric bands that would allow the sterile barrier to accommodate multiple geometries without breaking the sterile barrier. This would allow the sterile barrier to remain fitted to the device and also gather any undesirable pocketing or gathering that could negatively impact sterility.

In another aspect of the disclosed technology, a variable aluminum filter is placed between the X-ray source and the imaging detector. In a disclosed embodiment, a subsystem provides a variable thickness of aluminum equivalent filtration between the beam focal spot and the target anatomy. The filtration is required to be of a certain thickness to harden the x-ray beam from the most harmful lower energy x-rays, and the recommended thickness of aluminum equivalence is driven by the regulations found in 21 C.F.R. § 1020.30(m). These recommendations provide a half value layer reference coded to the kVp range of the x-ray source.

In the current state of the art, most manufacturers allow a single thickness of aluminum or material of aluminum equivalence to harden the beam that is sufficient for the entire range of x-ray potential to be produced, meaning the filtration is fixed at the thickness that complies with the highest possible tube potential. It is advantageous to provide variable thickness of filtration within the same limits provided by 21 C.F.R. as the image quality and the applied does may be further optimized. As best shown in FIG. 12, in one embodiment, a multiple stage filter is created by moving a fan shaped metal plate 83 between the primary beam and the patient anatomy. The fan includes plates of varying thickness to provide variable filtration. A fan plate is moved into the position most advantageous for image quality and radiation dose that is still compliant with the 21 C.F.R table requirements.

This variable aluminum equivalence could be accomplished by moving a variable thickness of aluminum in staged multiple plates, or by using varying materials such as copper, brass, aluminum, beryllium and just about any other metal that has a characteristic filtration of differing aluminum equivalence. The aluminum equivalence of a given material at a given thickness is readily measurable by a radiation survey meter equipped with a half value layer sensor capability. The differing aluminum equivalence materials could be drawn through the beam manually, or with a motor and pulley system, or with a linear actuator or a gear system or any other similar electronic or mechanical means of physically placing varying thicknesses of material or varying materials with different aluminum equivalences through the beam. Ideally the materials would be passed through in a perpendicular plane to the primary x-ray to source axis, but could be run through at any angle to the primary axis so as to create varying equivalent aluminum filtration by changing the position or material, or adding multiple plates of material. As will be appreciated, different X-ray tube voltages are needed to image different body part (e.g. higher voltages required for shoulders than hands). In one embodiment, a computer system reads the maximum voltage selected for the X-ray tube from a controller associated with a high voltage supply and selects the appropriate aluminum equivalence to be placed into the X-ray beam. The computer drives a motor or other actuator to position a fan plate with the correct equivalence into the beam path.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus. For example, a processor or controller in the fluoroscope can be configured or programmed to detect the SID and to alert a user to place the appropriate spacer in front of the X-ray source. In some embodiments, the processor is programmed to detect the space between the X-ray source and the transparent spacer 22 or the size of the spacer cone 52,56 that is installed in the fluoroscope to ensure compliance with the safety regulations before the processor enables the X-ray source to begin producing X-rays.

A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium also can be, or can be included in, one or more separate physical components or media (e.g., multiple CDs, disks, or other storage devices). The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include discrete digital hardware, special purpose logic circuitry, e.g., an FPGA (field programmable gate array) or an ASIC (application-specific integrated circuit). The apparatus also can include, in addition to hardware, code that creates an execution environment for the computer program in question.

To provide for interaction with a user, the fluoroscope may include a display device, e.g., an LCD (liquid crystal display), LED (light emitting diode), or OLED (organic light emitting diode) monitor, for displaying information to the user and a keyboard and a pointing device, e.g., a mouse or a trackball, by which the user can provide input to the processor associated with the system. In some implementations, a touch screen can be used to display information and to receive input from a user. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

From the foregoing, it will be appreciated that specific embodiments of the invention have been described herein for purposes of illustration, but that various modifications may be made without deviating from the scope of the invention. For example, in some embodiments, the size or shape of the C-arm can be adjusted (e.g. via a telescoping arm) to change the distance between the X-ray source and the receptor. Accordingly, the invention is not limited except as by the appended claims.

We claim:

1. A fluoroscope, comprising:
an X-ray source;
an X-ray receptor;
a support arm that supports the X-ray source and X-ray receptor in a spaced relation;
a mechanism for changing a distance between the X-ray source and the X-ray receptor;
means for maintaining a minimum source to skin distance (SSD) between the X-ray source and the skin of a patient disposed between the X-ray source and X-ray receptor; and
an X-ray transparent spacer between the X-ray source and the X-ray receptor, wherein the mechanism for changing the distance comprises a linkage that allows the X-ray source to move closer to, or farther away from, the X-ray receptor and wherein the means for maintaining the minimum source to skin distance comprises a cam surface on the linkage that moves the X-ray transparent spacer away from the X-ray source as the distance between the X-ray source and the X-ray receptor is increased.

2. The fluoroscope of claim 1, wherein the means for maintaining the minimum source to skin distance comprises a number of various sized spacers configured to be inserted between the X-ray source and the X-ray receptor depending on the distance between the X-ray source and the X-ray receptor.

3. The fluoroscope of claim 1, further comprising a sensor to detect a distance between the X-ray source and the X-ray receptor, wherein the means for maintaining the minimum source to skin distance comprises an actuator that moves the X-ray transparent spacer.

4. The fluoroscope of claim 3, wherein the sensor is optical.

5. The fluoroscope of claim 3, wherein the sensor is electrical.

6. The fluoroscope of claim 3, wherein the sensor is acoustic.

7. The fluoroscope of claim 1, further comprising (i) a sensor to detect a distance between the X-ray source and the X-ray receptor and a processor configured to provide instructions to a user to place the X-ray transparent spacer between the X-ray source and the X-ray receptor to maintain a minimum source to skin distance.

8. The fluoroscope of claim 7, wherein the X-ray transparent spacer is coded and the processor is configured to read a code on the transparent spacer before X-rays are produced by the fluoroscope.

9. A fluoroscope, comprising:
an X-ray source;
an X-ray receptor;
a support arm that supports the source and receptor in a spaced relation;
a mechanism for changing a distance between the source and the receptor;
a platform between the source and the receptor, the platform configured to support a portion of a body imaged by the fluoroscope;
an adjustment member that changes a minimum distance between the platform and the source, from a first value to a second value, as the distance between the source and the receptor exceeds a threshold; and
an X-ray transparent spacer between the X-ray source and the X-ray receptor, wherein the mechanism for changing the distance comprises a linkage that allows the X-ray source to move closer to, or farther away from, the X-ray receptor and wherein the adjustment member comprises a cam surface on the linkage that moves the X-ray transparent spacer away from the X-ray source as the distance between the X-ray source and the X-ray receptor is increased.

10. A fluoroscope, comprising:

a C-shaped support rail;

an X-ray imaging receptor coupled to the C-shaped support rail;

an imaging head including an X-ray source that is movably coupled to the C-shaped support rail such that the imaging head can be moved to a first position farthest away from the imaging receptor or to a second position closest to the imaging receptor;

a spacer that is extendable from the imaging head;

position sensors to detect the position of the imaging head with respect to the imaging receptor and whether the spacer is extended from the imaging head; and a processor that is programmed to inhibit operation of the X-ray source based on signals from the position sensors that indicate that the imaging head is at the first position farthest away from the imaging receptor and the spacer is not extended wherein the spacer is an X-ray transparent spacer between the X-ray source and the X-ray receptor, wherein a mechanism for changing the distance comprises a linkage that allows the X-ray source to move closer to, or farther away from, the X-ray receptor and wherein a means for maintaining the minimum source to skin distance comprises a cam surface on the linkage that moves the X-ray transparent spacer away from the X-ray source as the distance between the X-ray source and the X-ray receptor is increased.

11. The fluoroscope of claim 10, wherein the imaging head is secured to the C-shaped support rail with a hinge and the imaging sensors include a micro-switch having a contact that is configured to ride against a surface of the hinge and seat within a recess on a surface of the hinge to open the micro-switch when the imaging head is in one of the first or the second positions.

12. The fluoroscope of claim 10, wherein the imaging head is secured to the C-shaped support rail with a hinge and the imaging sensors include a micro-switch having a contact that is configured to ride in a slot on a surface of the hinge and be closed by a ramp on the surface of the hinge when the imaging head is in one of the first or second positions.

* * * * *